(12) United States Patent
Kamen et al.

(10) Patent No.: US 8,632,513 B2
(45) Date of Patent: Jan. 21, 2014

(54) SYSTEMS AND METHODS FOR REMOVING INGESTED MATERIAL FROM A STOMACH

(75) Inventors: Dean Kamen, Bedford, NH (US); Kevin L. Grant, Litchfield, NH (US); Eric M. Soederberg, Bedford, NH (US); David E. Altobelli, Hollis, NH (US); David Flynn, Manchester, NH (US); Kenneth S. Solovay, Weston, FL (US); Samuel Klein, Clayton, MO (US)

(73) Assignee: Aspire Bariatrics, Inc., King of Prussia, PA (US)

( * ) Notice: Subject to any disclaimer, the term of this patent is extended or adjusted under 35 U.S.C. 154(b) by 154 days.

(21) Appl. No.: 13/078,838

(22) Filed: Apr. 1, 2011

(65) Prior Publication Data

US 2011/0190719 A1    Aug. 4, 2011

Related U.S. Application Data

(63) Continuation of application No. 11/890,274, filed on Aug. 3, 2007, now Pat. No. 8,002,758, and a continuation-in-part of application No. 11/675,527, filed on Feb. 15, 2007, now Pat. No. 7,648,479.

(60) Provisional application No. 60/821,333, filed on Aug. 3, 2006.

(51) Int. Cl.
| *A61M 1/00* | (2006.01) |
| *A61M 39/00* | (2006.01) |
| *A61M 39/22* | (2006.01) |
| *A61F 5/44* | (2006.01) |

(52) U.S. Cl.
USPC ........ 604/320; 604/8; 604/9; 604/10; 604/19; 604/27; 222/548; 222/555

(58) Field of Classification Search
USPC ........... 604/320, 9, 10, 19, 27, 30, 32, 35, 36, 604/48, 513, 93.01, 263, 264, 276, 278, 3, 604/17, 327, 332, 335; 222/548
See application file for complete search history.

(56) References Cited

U.S. PATENT DOCUMENTS 2,533,915 A * 12/1950 Brooks .......................... 222/513
2,933,140 A     4/1960 Gagliardo
(Continued)

FOREIGN PATENT DOCUMENTS

DE    10239443    3/2004
EP    0059044    9/1982
(Continued)

OTHER PUBLICATIONS

Annex to form PCT/ISA/206 Communication Relating to the Results of the Partial International Search for International Application No. PCT/US2007/015479 dated Dec. 7, 2007, 2 pages.
(Continued)

*Primary Examiner* — Adam Marcetich
(74) *Attorney, Agent, or Firm* — Woodcock Washburn, LLP

(57) ABSTRACT

When a patient is fitted with an external gastrostomy connection to the stomach, ingested food can be removed through the gastrostomy connection using a pump-based or siphon-based system to achieve weight loss. The process of removing ingested food can be improved by alternating the infusion of liquid into the stomach with the removal of material from the stomach. Optionally, stomach acid may be captured and returned to the stomach. Optionally, nutritional supplements or medicines may be added to the infused liquid. Optionally, a flush mount connectorized system with a built in valve may be used to simplify the interface with the gastrostomy hardware that remains installed in the patient. Optionally, the system may be configured to disable itself from further use after a triggering event (e.g., the passage of time or a predetermined number of uses) has occurred.

38 Claims, 18 Drawing Sheets

(56) References Cited

U.S. PATENT DOCUMENTS

| | | | |
|---|---|---|---|
| 3,066,672 A | 12/1962 | Crosby, Jr. et al. | |
| 3,144,868 A | 8/1964 | Jascalevich | |
| 3,214,069 A | 10/1965 | Dike | |
| 3,232,578 A | 2/1966 | Cousins | |
| 3,384,342 A | 5/1968 | Passer | |
| 3,506,237 A | 4/1970 | Tometsko | |
| 3,598,150 A | 8/1971 | Nolan | |
| 3,752,158 A | 8/1973 | Kariher | |
| 3,860,000 A | 1/1975 | Wootten et al. | |
| 3,884,808 A | 5/1975 | Scott | |
| 3,924,625 A | 12/1975 | Peterson | |
| 4,082,095 A | 4/1978 | Mendelson et al. | |
| 4,116,589 A | 9/1978 | Rishton | |
| 4,189,795 A | 2/1980 | Conti et al. | |
| 4,190,173 A * | 2/1980 | Mason et al. | 220/203.05 |
| 4,315,509 A | 2/1982 | Smit | |
| 4,315,513 A | 2/1982 | Nawash et al. | |
| 4,344,435 A | 8/1982 | Aubin | |
| 4,356,824 A | 11/1982 | Vazquez | |
| 4,381,765 A | 5/1983 | Burton | |
| 4,393,873 A | 7/1983 | Nawash et al. | |
| 4,393,875 A | 7/1983 | O'Boyle et al. | |
| 4,449,972 A | 5/1984 | Kruger | |
| 4,464,175 A | 8/1984 | Altman et al. | |
| 4,525,156 A | 6/1985 | Benusa et al. | |
| 4,538,653 A | 9/1985 | Shea et al. | |
| 4,551,130 A | 11/1985 | Herbert et al. | |
| 4,553,960 A | 11/1985 | Lazarus et al. | |
| 4,555,242 A * | 11/1985 | Saudagar | 604/103.08 |
| 4,642,092 A | 2/1987 | Moss | |
| 4,668,225 A | 5/1987 | Russo et al. | |
| 4,685,901 A | 8/1987 | Parks | |
| 4,723,547 A | 2/1988 | Kullas et al. | |
| 4,790,812 A | 12/1988 | Hawkins, Jr. et al. | |
| 4,804,375 A | 2/1989 | Robertson | |
| 4,822,338 A | 4/1989 | Longmore et al. | |
| 4,834,724 A | 5/1989 | Geiss et al. | |
| 4,863,438 A * | 9/1989 | Gauderer et al. | 604/247 |
| 4,899,747 A | 2/1990 | Garren et al. | |
| 4,935,009 A | 6/1990 | Caldwell et al. | |
| 5,071,405 A | 12/1991 | Piontek et al. | |
| 5,074,850 A | 12/1991 | Chion | |
| 5,098,378 A | 3/1992 | Piontek et al. | |
| 5,234,454 A | 8/1993 | Bangs | |
| 5,259,399 A | 11/1993 | Brown | |
| 5,263,367 A | 11/1993 | Pippert | |
| 5,306,300 A | 4/1994 | Berry | |
| 5,345,949 A | 9/1994 | Shlain | |
| 5,358,488 A | 10/1994 | Suriyapa | |
| 5,379,926 A | 1/1995 | Mueller et al. | |
| 5,411,022 A | 5/1995 | McCue et al. | |
| 5,417,664 A | 5/1995 | Felix et al. | |
| 5,468,240 A | 11/1995 | Gentelia et al. | |
| 5,507,419 A | 4/1996 | Martin et al. | |
| 5,520,307 A | 5/1996 | Miller et al. | |
| 5,520,634 A | 5/1996 | Fox et al. | |
| 5,520,662 A | 5/1996 | Moss | |
| 5,527,280 A | 6/1996 | Goelz | |
| 5,549,657 A | 8/1996 | Stern et al. | |
| 5,601,213 A | 2/1997 | Daniello | |
| 5,601,604 A | 2/1997 | Vincent | |
| 5,618,296 A | 4/1997 | Sorensen et al. | |
| 5,716,347 A | 2/1998 | Gibbs et al. | |
| 5,730,322 A | 3/1998 | Iba et al. | |
| 5,741,287 A | 4/1998 | Alden et al. | |
| 5,743,468 A | 4/1998 | Laidler | |
| 5,868,141 A | 2/1999 | Ellias | |
| 5,871,475 A | 2/1999 | Frassica | |
| 5,895,377 A | 4/1999 | Smith et al. | |
| 5,897,530 A | 4/1999 | Jackson | |
| 5,925,075 A | 7/1999 | Myers et al. | |
| 5,927,604 A | 7/1999 | Laidler | |
| 5,972,399 A | 10/1999 | Lapre et al. | |
| 5,989,231 A | 11/1999 | Snow et al. | |
| 6,019,746 A | 2/2000 | Picha et al. | |
| 6,039,251 A | 3/2000 | Holowko et al. | |
| 6,048,329 A | 4/2000 | Thompson et al. | |
| 6,070,624 A * | 6/2000 | Bilbrey et al. | 141/346 |
| 6,077,243 A | 6/2000 | Quinn | |
| 6,077,250 A | 6/2000 | Snow et al. | |
| 6,152,911 A | 11/2000 | Gainnoble | |
| 6,210,347 B1 | 4/2001 | Forsell | |
| 6,245,039 B1 | 6/2001 | Brugger et al. | |
| 6,315,170 B1 | 11/2001 | Thomson et al. | |
| 6,322,495 B1 | 11/2001 | Snow et al. | |
| 6,328,720 B1 | 12/2001 | McNally et al. | |
| 6,341,737 B1 | 1/2002 | Chang | |
| 6,378,735 B1 * | 4/2002 | Chu | 222/158 |
| 6,381,495 B1 | 4/2002 | Jenkins | |
| 6,447,472 B1 | 9/2002 | Moss | |
| 6,453,907 B1 | 9/2002 | Forsell | |
| 6,454,785 B2 | 9/2002 | De Hoyos Garza | |
| 6,506,179 B1 | 1/2003 | Tiefenthal et al. | |
| 6,511,490 B2 | 1/2003 | Robert | |
| 6,533,734 B1 | 3/2003 | Corley, III et al. | |
| 6,572,629 B2 | 6/2003 | Kalloo et al. | |
| 6,579,301 B1 | 6/2003 | Bales et al. | |
| 6,585,681 B2 | 7/2003 | Brugger et al. | |
| 6,615,084 B1 | 9/2003 | Cigaina | |
| 6,626,884 B1 | 9/2003 | Dillon et al. | |
| 6,627,206 B2 | 9/2003 | Lloyd | |
| 6,645,183 B2 | 11/2003 | Christensen et al. | |
| 6,659,974 B1 | 12/2003 | Moss | |
| 6,666,853 B2 | 12/2003 | Chu et al. | |
| 6,691,981 B1 | 2/2004 | Hart | |
| 6,736,336 B2 | 5/2004 | Wong | |
| 6,743,193 B2 | 6/2004 | Brugger et al. | |
| 6,752,790 B2 | 6/2004 | Coombs | |
| 6,755,869 B2 | 6/2004 | Geitz | |
| 6,757,957 B2 | 7/2004 | McClean et al. | |
| 6,758,836 B2 | 7/2004 | Zawacki | |
| 6,902,541 B2 | 6/2005 | McNally et al. | |
| 6,923,786 B2 | 8/2005 | Rouns et al. | |
| 6,976,980 B2 | 12/2005 | Brenner et al. | |
| 7,025,791 B2 | 4/2006 | Levine et al. | |
| 7,174,916 B2 | 2/2007 | Chang | |
| 7,175,612 B2 | 2/2007 | Felix et al. | |
| 7,383,852 B2 | 6/2008 | Pittaway et al. | |
| 7,434,594 B1 | 10/2008 | Robbins et al. | |
| 7,524,445 B2 | 4/2009 | Duran et al. | |
| 7,641,648 B2 | 1/2010 | Bouphavichith et al. | |
| 7,648,479 B2 | 1/2010 | Solovay et al. | |
| 7,682,346 B2 | 3/2010 | McNally et al. | |
| 7,708,724 B2 | 5/2010 | Weston | |
| 7,713,246 B2 | 5/2010 | Shia et al. | |
| 7,740,624 B2 | 6/2010 | Klein et al. | |
| 7,815,629 B2 | 10/2010 | Klein et al. | |
| 8,002,727 B2 | 8/2011 | Brugger et al. | |
| 8,002,758 B2 | 8/2011 | Kamen et al. | |
| 8,062,285 B2 | 11/2011 | Langloss et al. | |
| 2001/0049490 A1 | 12/2001 | Slanda et al. | |
| 2002/0077604 A1 | 6/2002 | Willis et al. | |
| 2002/0115966 A1 | 8/2002 | Christensen et al. | |
| 2002/0193753 A1 | 12/2002 | Rouns et al. | |
| 2003/0032932 A1 * | 2/2003 | Stout | 604/385.01 |
| 2003/0040808 A1 | 2/2003 | Stack et al. | |
| 2003/0069553 A1 | 4/2003 | Talamonti | |
| 2003/0097097 A1 * | 5/2003 | Scagliarini et al. | 604/246 |
| 2003/0109935 A1 | 6/2003 | Geitz | |
| 2003/0149395 A1 | 8/2003 | Zawaki | |
| 2003/0158539 A1 * | 8/2003 | Bouphavichith et al. | 604/533 |
| 2003/0208015 A1 | 11/2003 | Mault et al. | |
| 2003/0225369 A1 | 12/2003 | McMichael | |
| 2004/0055948 A1 | 3/2004 | Blum et al. | |
| 2004/0082909 A1 | 4/2004 | Shia et al. | |
| 2004/0220516 A1 | 11/2004 | Solomon et al. | |
| 2005/0277900 A1 | 12/2005 | Klein et al. | |
| 2005/0283130 A1 | 12/2005 | Klein et al. | |
| 2006/0079853 A1 | 4/2006 | Christensen et al. | |
| 2006/0135914 A1 | 6/2006 | Chu et al. | |
| 2006/0147665 A1 | 7/2006 | Duran et al. | |
| 2006/0264983 A1 | 11/2006 | Holsten et al. | |
| 2006/0270970 A1 | 11/2006 | Moss | |
| 2006/0289011 A1 | 12/2006 | Helsel | |

(56) References Cited

U.S. PATENT DOCUMENTS

| | | | |
|---|---|---|---|
| 2007/0187406 | A1 | 8/2007 | Nobile et al. |
| 2008/0033364 | A1 | 2/2008 | Kamen et al. |
| 2008/0091146 | A1 | 4/2008 | Solovay et al. |
| 2010/0106130 | A1 | 4/2010 | Solovay et al. |
| 2010/0106131 | A1 | 4/2010 | Klein et al. |
| 2010/0241090 | A1 | 9/2010 | Klein et al. |
| 2011/0082442 | A1 | 4/2011 | Solovay et al. |
| 2011/0178480 | A1 | 7/2011 | Solovay et al. |

FOREIGN PATENT DOCUMENTS

| | | |
|---|---|---|
| EP | 0194980 | 9/1986 |
| EP | 0691868 | 6/2002 |
| EP | 1374930 | 1/2004 |
| EP | 2389962 | 11/2011 |
| EP | 2412393 | 2/2012 |
| FR | 2630011 | 10/1989 |
| JP | 62-224358 | 10/1987 |
| JP | 3-018378 | 1/1991 |
| JP | 04-002361 | 1/1992 |
| JP | 04-198680 | 7/1992 |
| JP | 05-115429 | 5/1993 |
| JP | 05-317325 | 12/1993 |
| JP | 07-096030 | 4/1995 |
| JP | 08-196621 | 8/1996 |
| JP | 08-266546 | 10/1996 |
| JP | 2001-29434 | 2/2001 |
| JP | 2005-522269 | 7/2005 |
| JP | 2006-508711 | 3/2006 |
| JP | 2006-102539 | 4/2006 |
| JP | 2009-542349 | 12/2009 |
| JP | 2009-545383 | 12/2009 |
| WO | WO 94/15655 | 7/1994 |
| WO | WO 99/25418 | 5/1999 |
| WO | WO 01/68007 | 9/2001 |
| WO | WO 02/32477 | 4/2002 |
| WO | WO 03/086247 | 10/2003 |
| WO | WO 2004/098692 | 11/2004 |
| WO | WO 2005/060869 | 7/2005 |
| WO | WO 2006/014496 | 2/2006 |
| WO | WO 2006/020441 | 2/2006 |
| WO | WO 2006/022709 | 3/2006 |
| WO | WO 2006/088419 | 8/2006 |
| WO | WO 2008/005496 | 1/2008 |
| WO | WO 2008/019082 | 2/2008 |
| WO | WO 2011/031679 | 3/2011 |

OTHER PUBLICATIONS

Brolin, "Bariatric surgery and long-term control of morbid obesity", JAMA, Dec. 2002, 288(22), 2793-2796.

Buchwald et al., "Bariatric Surgery, a Systematic Review and Meta-Analysis", JAMA, Oct. 13, 2004, 292(14), 1724-1737.

Cantor et al., "Book Review of Animal Models of Human Psychology: Critique of Science Ethics and Policy by Kenneth J. Shapiro", Animals Agenda, May/Jun. 1998, 18.3, p. 36.

Doenz et al., "Versatility of the Proximal Cope Loop Catheter", American Journal of Roentgenolog, Jan. 1989, 152, 1 page.

Duszak, "Percutaneous Gastrostomy and Jejunostomy", eMedicine Instant access to the Minds of Medicine, http://www.ernedicine.com/radio/topic798.htm, Jul. 8, 2005, 18 pages.

Felsher et al., "Decompressive Percutaneous Endoscopic Gastrotomy in Nonmalignant Disease", The American Journal of Surgery, 2004, 187, 254-256.

Flegal et al., "Prevalence and Trends in Obesity Among US Adults, 1999-2000", JAMA, Oct. 9, 2002, 288(1), 1723-1727.

Gehman et al., "Percutaneous Gastrojejunostomy with a Modified Cope Loop Catheter", American Journal of Roentgenology, Jul. 1990, 155, 79-80.

Goldstein, "Beneficial Health Effects of Modest Weight Loss", International Journal of Obesity and Related Metabolic Disorders: Journal of the International Association for the Study of Obesity, Jun. 1992, 16(6), 397-415.

Gray et al., "Modified Catheter for Percutaneous Gastrojejunostomy", Radiology, Oct. 1989, 173(1), 276-278.

Harper et al., "The Long Term Outcome in Crohn's Disease", Am. Soc. Gastrointestinal Endoscopy, Mar. 1987, 30(3), 174-179.

Herman et al., "Percutaneous Endoscopic Gastrostomy for Decompression of the Stomach and Small Bowel", Gastrointestinal Endoscopy, May 1992, 38(3), 314-318.

Lorentzen et al., "Percutaneous Gastrostomy Guided by Ultrasound and Fluroscopy", ACTA Radiologica, 1995, 36, 159-162.

Luck et al., "Laprascoic Gastrostomy: Towards the Ideal Techniques", Aust. N.Z. J. Surg., Apr. 1998, 68, 281-283.

Meissner, "Adjuvant Surgical Decompression Gastrostomy: Audit of a Procedure Coming of Age", Hepatogastroenterology, Mar.-Apr. 2004, 51(56), 462-464.

Michaud et al., "Gastrostomy as a Decompression Technique in Children with Chronic Gastrointestinal Obstruction", J. Pediatr. Gastroenterol. Nutr., Jan. 2001, 32(1), 82-85.

Nassif, "Efficient Decompression and Immediate Enteral Hyperaliment via Gastrostomy as an Adjunct to Gastroplasty", Obes Surg., Mar. 1991, 1(1), 99-102.

Ozmen et al., "Percutaneous Radiological Gastrrostomy", European Journal of Radiology, Sep. 2002, 43(3), 186-195.

Pearce et al., "The 'cut and push' Method of Percutaneous Endoscopic Gastrostomy Tube Removal", Clinical Nutrition, Apr. 2000, 19(2),133-135.

Shapiro, "Animal Models of Human Psychology: Critique of Science, Ethics, and Policy", Seattle: Hogrefe and Huber, Apr. 1998, Chapter 4, 111-211.

Shike et al., "An Active Esophageal Prosthesis", Gastrointestinal Endoscopy, Jan. 1995, 41(1), 64-67.

Shike et al., "Combined Gastric Drainage and Jejunal feeding through a Percutaneous Endoscopic Stoma", Gastrointestinal Endoscopy, May-Jun. 1990, 36(3), 290-292.

Shike et al., "External Biliary Duodenal Drainage through a Percutaneous Endoscopic Duodenostomy", Gastrointestinal Endoscopy, Mar.-Apr. 1989, 35(2), 104-105.

Shike et al., "Skin-level Gastrostomies and Jejunostomies for Long-Term Enter Feeding", JPEN J Parenter Enteral Nurt., Nov.-Dec. 1989, 13(6), 648-650.

Shike, "Percutaneous Endoscopic Stomas for Enteral Feeding and Drainage", Oncology (Williston Park, Discussion 44), Jan. 1995, 9(1), 39-44.

Shike, "Percutaneous Endoscopic Gastrostomy and Jejunostomy for long-term feeding in Patients with Cancer of the head and neck", Otolaryngology Head and Neck Surgery, Nov. 1989, 101(5), 549-554.

Suazo-Barahona et al., "Obesity: A Risk Factor for Severe Acute Biliary and Alcoholic Pancreatitis". Am. J. Gastroenterology, Aug. 1998, 98(3), 1324-1328.

Thornton et al., "Percutaneous Radiologic Gastrostomy With and Without T-Fastener Gastroplexy: A Randomized Comparison Study", Cardiovasc. Interven. Rad., Nov. 2002, 25, 467-471.

European Patent Application No. EP 11179953: Extended European Search Report dated Jan. 20, 2012, 7 pages.

Japanese Application No. 2009-518367: Notice of Reasons for Rejection dated May 15, 2012, 5 pages (English Translation Attached).

Japanese Application No. 2009-522889: Notice of Reasons for Rejection dated May 22, 2012, 7 pages (English Translation Attached).

International Patent Application No. PCT/US2012/051995: International Search Report and Written Opinion dated Apr. 12, 2013, 22 pages.

\* cited by examiner

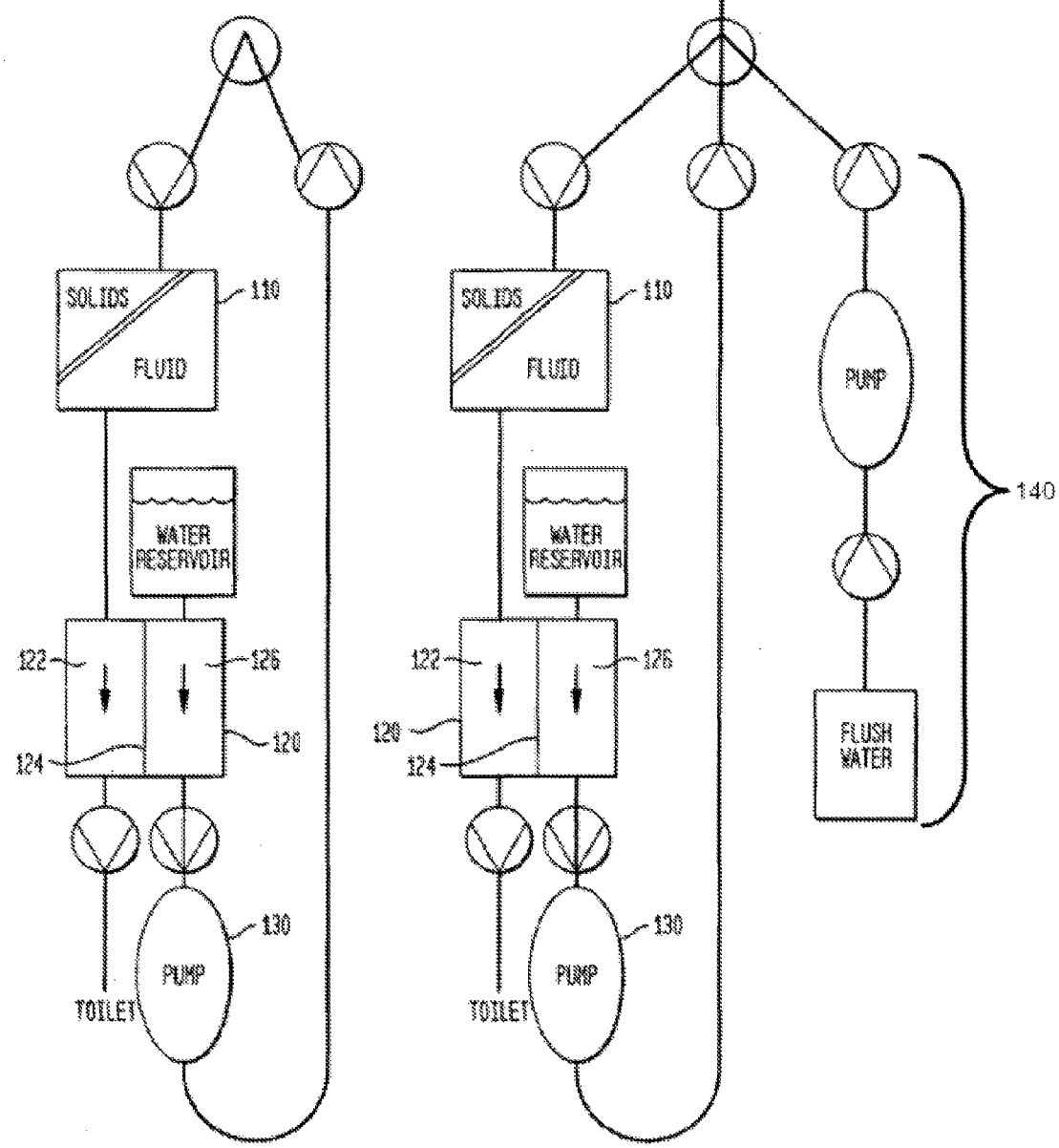

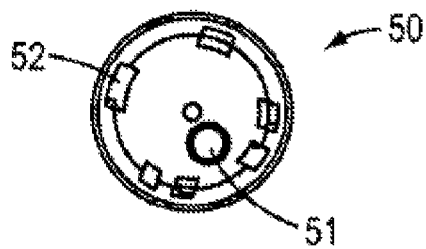
FIG. 9B     FIG. 9C
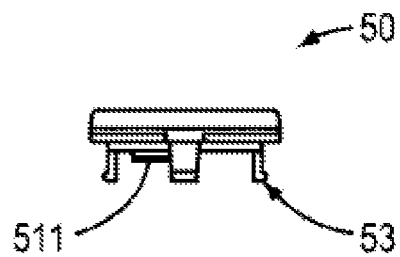
FIG. 9A
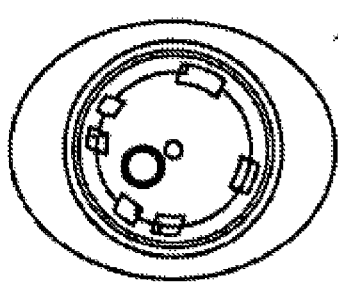
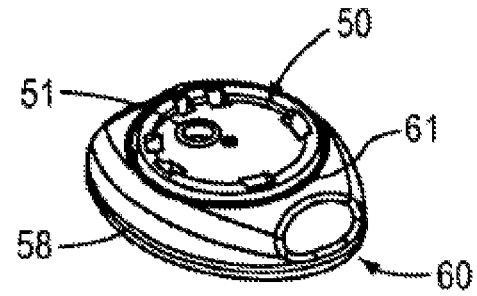
FIG. 10B     FIG. 10C
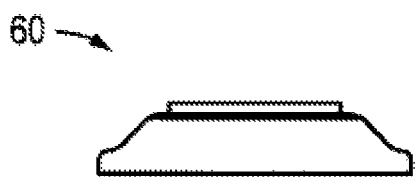
FIG. 10A

SECTION A-A

SECTION D-D

SYSTEMS AND METHODS FOR REMOVING INGESTED MATERIAL FROM A STOMACH

CROSS REFERENCE TO RELATED APPLICATIONS

This application is a continuation of pending U.S. patent application Ser. No. 11/890,274 filed Aug. 3, 2007 which claims the benefit of and priority to U.S. Provisional Application No. 60/821,333, filed Aug. 3, 2006, now expired, U.S. Pat. No. 7,648,479 which issued Jan. 19, 2010, originally U.S. patent application Ser. No. 11/675,527, filed Feb. 15, 2007.

BACKGROUND OF THE INVENTION

The invention generally relates to removing ingested material from a stomach of a patient, and the primary intended fields of the invention are facilitating weight loss and preventing weight gain.

BRIEF SUMMARY OF THE INVENTION

In one aspect of the invention, food that has been ingested is removed from the patient's stomach via a gastrostomy tube using a siphon action. In another aspect of the invention, food that has been ingested is removed from the patient's stomach via a gastrostomy tube, and the removal of food is facilitated by infusing fluid into the patient's stomach via the gastrostomy tube. In another aspect of the invention, matter that has been ingested is removed from the patient's stomach via a gastrostomy tube, and stomach acid is separated from the removed matter and returned to the patient's stomach. In another aspect of the invention, matter that has been ingested is removed from the patient's stomach via a gastrostomy tube, and the system is configured to disable itself from further use after the occurrence of a triggering event (e.g., the passage of time or a predetermined number of uses).

BRIEF DESCRIPTION OF THE DRAWINGS

FIG. 7A schematically shows an embodiment of a system for removing ingested material from a stomach, filtering select gastric contents, and returning filtered fluid to the stomach.

FIG. 7B schematically shows an embodiment of a system for removing ingested material from a stomach, filtering select gastric contents, and returning filtered fluid and water to the stomach.

FIGS. 9A, 9B, and 9C show side, top, and isometric views of a skin connector valve assembly for the embodiment shown in FIGS. 8A-8C.

FIGS. 10A, 10B, and 10C show side, top, and isometric views of an assembled flush skin connector for the embodiment shown in FIGS. 8A-8C.

DETAILED DESCRIPTION OF THE PREFERRED EMBODIMENTS

This application discloses methods and apparatuses for removing material from a patient. In the exemplary embodiment disclosed herein, the methods and apparatuses are used for removing ingested material from a patient's stomach in patients that have been fitted with a gastrostomy tube. Examples of suitable gastrostomy tubes are described in U.S. Patent Application Publication Nos. US 2004/0220516, US 2005/0277900 and US 2005/0283130, each of which is incorporated herein by reference. Additional gastrostomy tubes are described in U.S. Provisional Patent Application 60/806,556, which is also incorporated herein by reference.

The primary contemplated use for the methods and apparatuses described herein is achieving weight loss in obese or overweight people. Although the exemplary embodiments are described herein in the context of removing ingested material from a patient's stomach, the methods and apparatus can also be used for removal of a variety of fluids from a patient (with, when necessary, appropriate modifications that will be apparent to persons skilled in the relevant arts).

Figure 1:
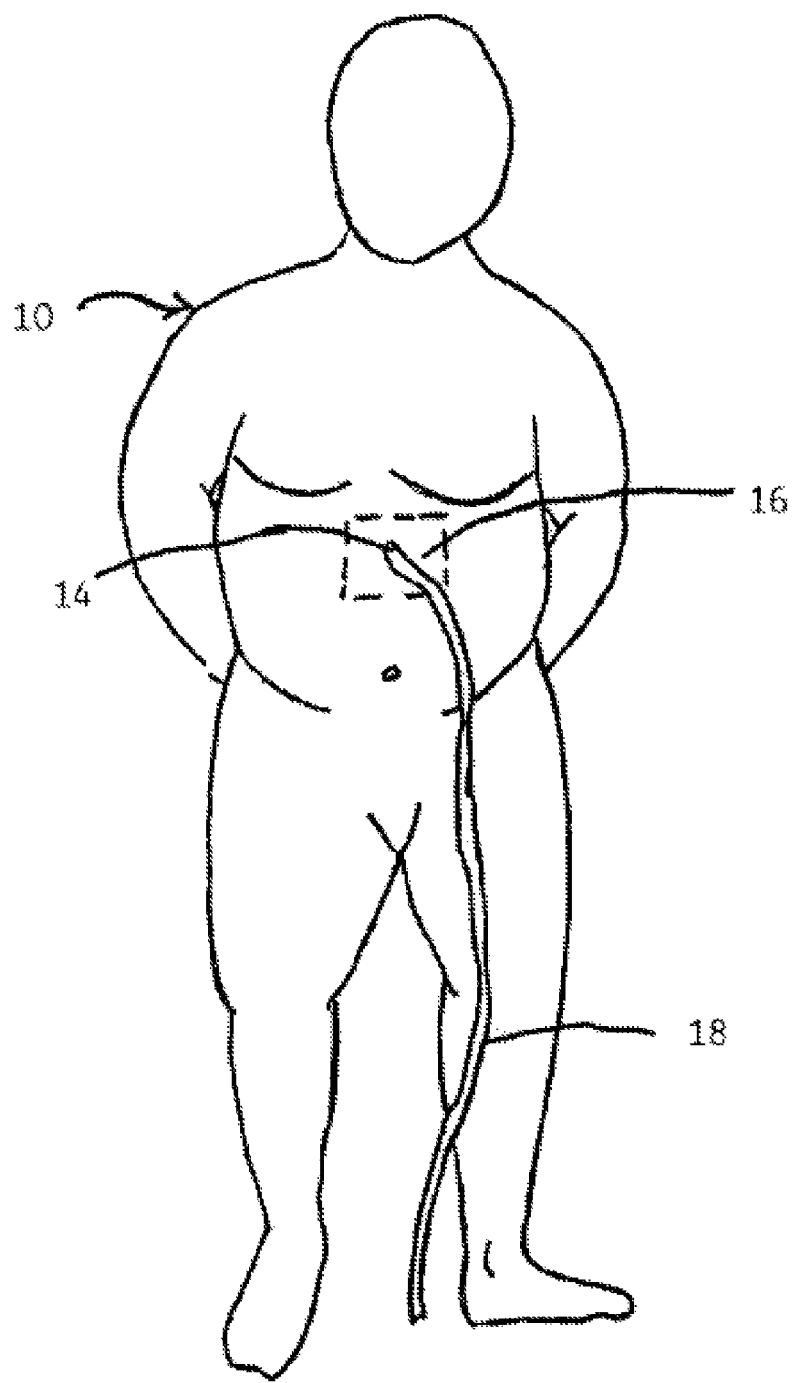
FIG. 1 is a schematic representation of an embodiment of the invention for removing ingested material from a patient's stomach.
Figure 8A:
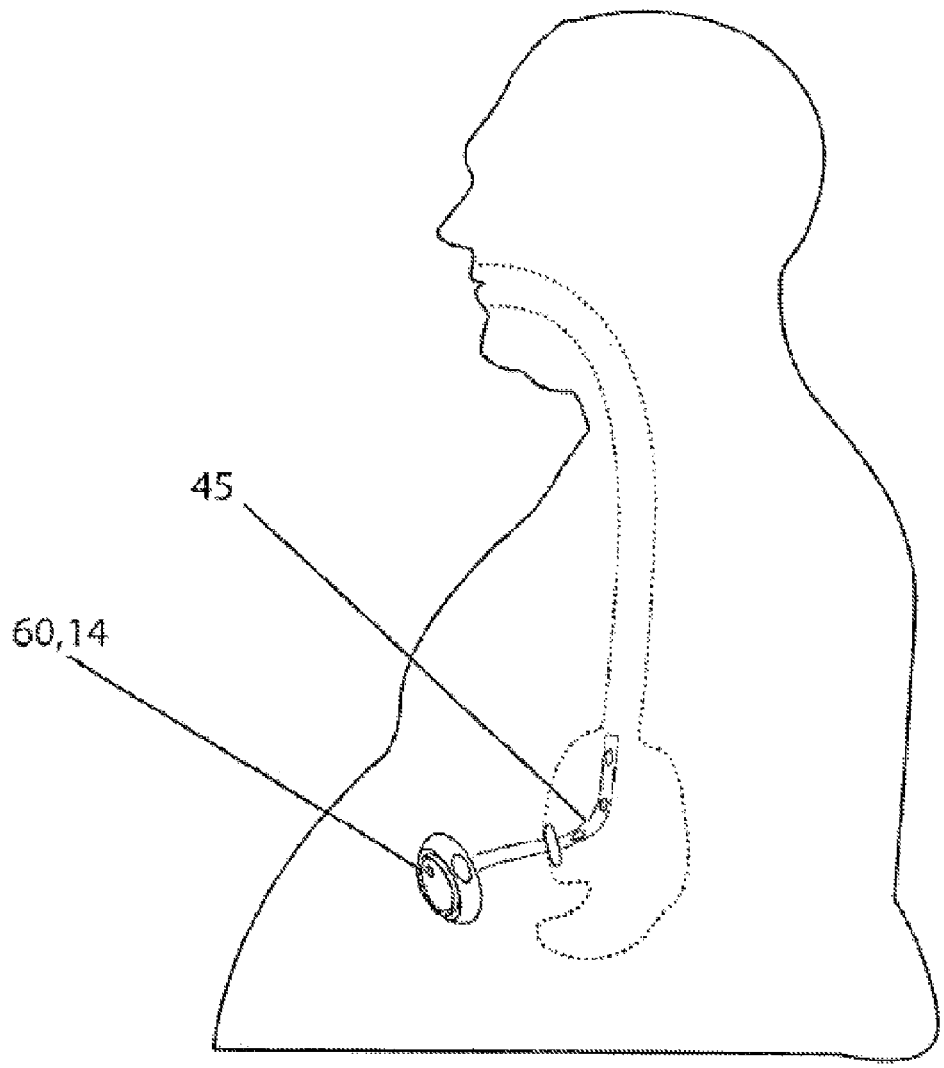
FIG. 8A shows a patient with a skin connector coupled with a gastrostomy tube that is inserted into the stomach.
Figure 8B:
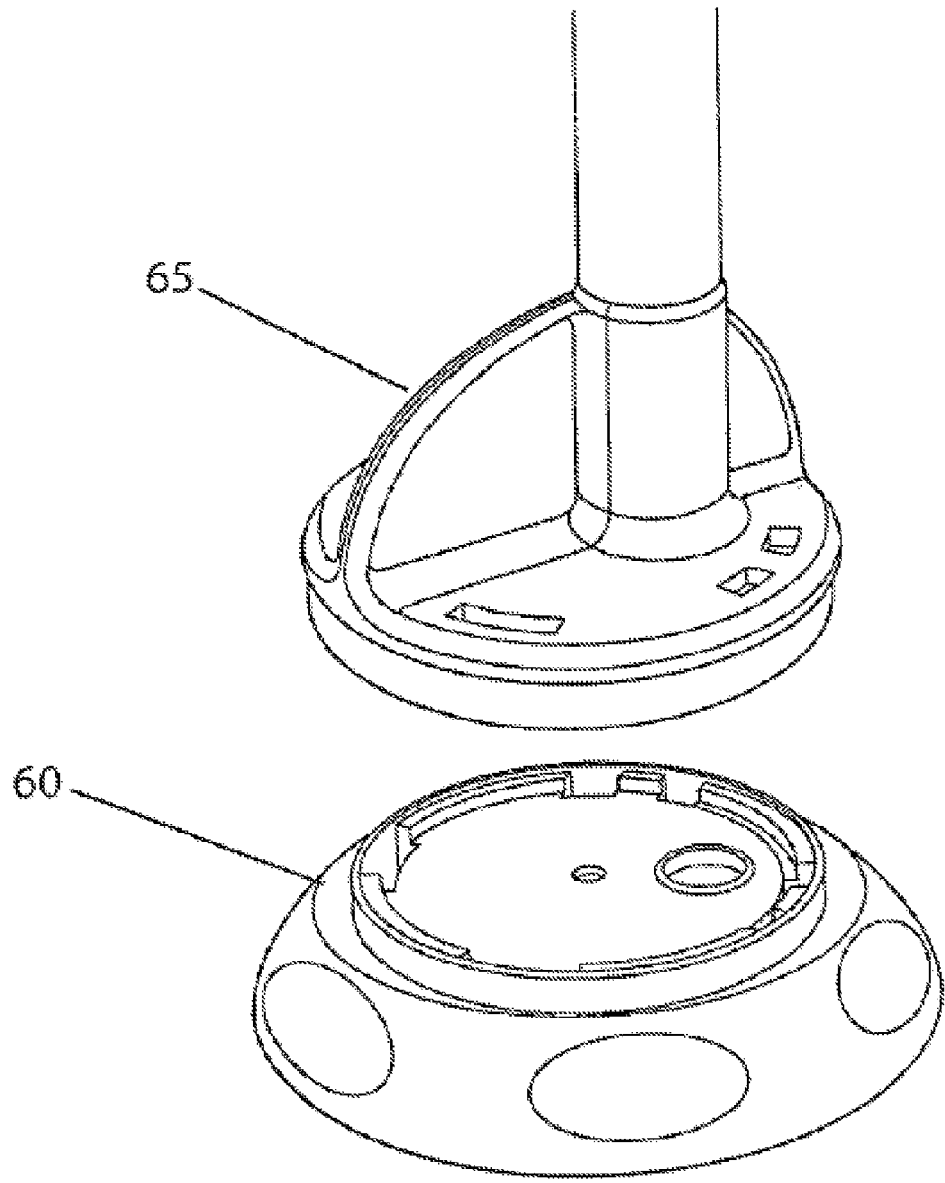
FIG. 8B shows a view of the skin connector prior to mating with a tube connector.
Figure 8C:
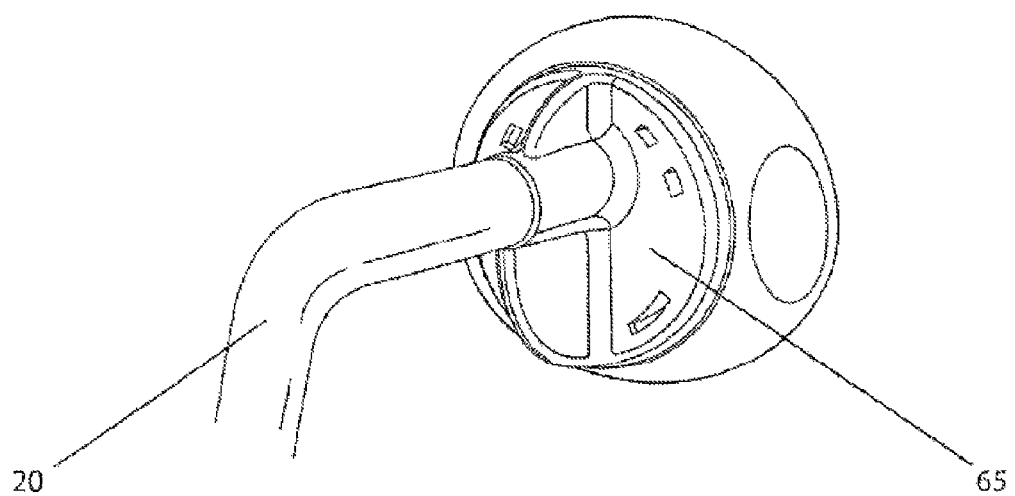
FIG. 8C shows a view of the skin connector mated with a tube connector.
Figure 11A:
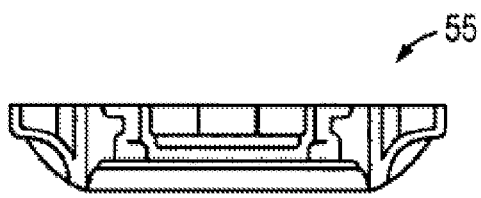
FIGS. 11A, 11B, 11C, and 11D show side, top, and isometric views of a skin connector flange assembly for the embodiment shown in FIGS. 8A-8C.
Figure 11C:
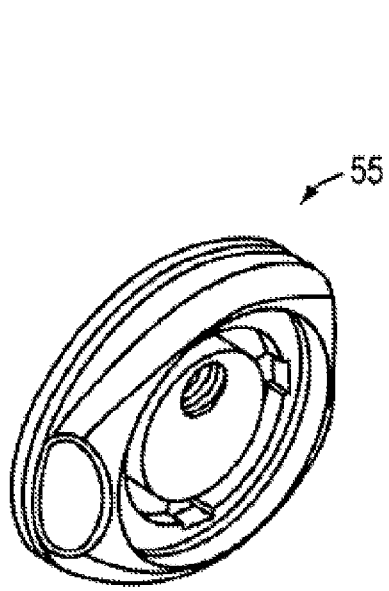
Figure 11B:
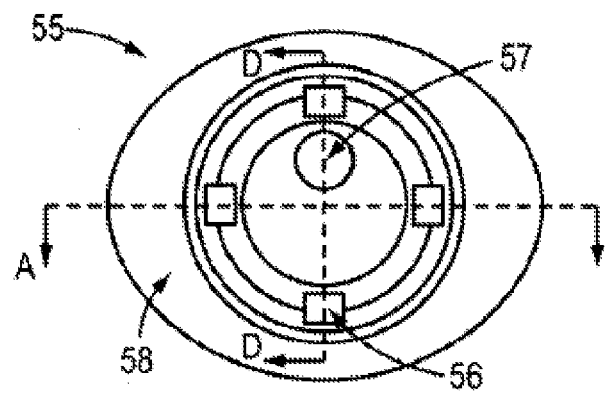
Figure 11D:
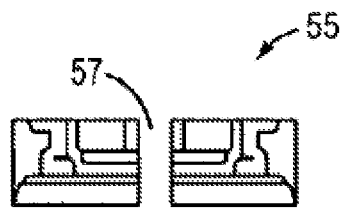

FIG. 1 shows a patient 10 that is fitted with a gastrostomy tube with a system for removing ingested material from a stomach. An example of such a gastrostomy tube 45 is shown in FIG. 8A. The gastrostomy tube 45 interfaces with the outside world via connection 14, so the system communicates with the gastrostomy tube 45 through that connection. The system preferably includes an assembly 16 for infusing fluid into the stomach through the connection 14 in a manner permitting the fluid to mix with the ingested material or, for use in priming the system when desired, and a drain line 18 for draining content of the stomach received from the connection 14.

The drain line 18 may be in communication with the assembly 16, as shown. In alternative embodiments (not shown), the drain line 18 may be implemented independent of the assembly 16. For example, one line may be used to drain content of the stomach through the connection 14 and another line may infuse the fluid into the stomach through the connection. The system preferably includes a patient line 20 in communication with the assembly 16 and the connection 14 to the patient 10, and the patient line 20 preferably has a suitable connector at its upper end that mates with the connection 14. In alternative embodiments (not shown), the assembly 16 may be coupled directly to the external gastrostomy connection 14 without using an intermediate patient line. The assembly 16 may include a fluid source and may optionally include a valve arrangement and/or one or more pumps as described in more detail below.

In operation, the system is connected up to the connection 14 to remove the contents of the stomach via the connection. In some embodiments, the removal may be accomplished by pumping the stomach contents out via the connection 14. In alternative embodiments, this removal is accomplished by setting up a siphon system so that the contents of the stomach can be siphoned out of the patient's stomach.

In siphon-based systems, the drain line 18 preferably has a length in excess of 25 cm in order to create a pressure differential that is sufficient to form an effective, efficient siphon that can gently and passively drain content from the stomach. However, in alternative embodiments, the drain line 18 can be of a length less than 25 cm. Note that when the patient is standing, the overall siphon system is measured from the lowest point in the tube or line that is inserted into the stomach to the end of the drain line 18. Optionally, the siphon system may be designed to be long enough to run from the stomach of a standing patient to a position proximate to a floor-based disposal arrangement, such as a toilet or waste container. The drain line may include a siphon tube made from flat, collapsible tubing or other flexible tubing. Silicon is a suitable material for the patient line 20 and the drain line 18. However, in alternative embodiments, the patient line 20 can be made from any material known and used in the art of tubes or any material that could be used to impart the necessary function of the patient line 20.

In some situations (e.g., when the patient has drank a significant amount of liquids), an effective siphon effect can be achieved without infusing any liquids into the patient's stomach. In other situations, however, it may be necessary to add additional fluid into the patient's stomach to help start up the siphoning, so that the ingested material can be effectively removed from the patient's stomach. This may be done by having the patient drink additional fluids or by infusing additional fluid into the stomach through the connection 14.

In many cases, a single siphoning operation will be insufficient to remove the desired amount of ingested material from the patient's stomach. In those cases, it is desirable to introduce additional liquid into the stomach so that one or more additional siphoning operations can be done. A preferred approach for introducing additional liquid into the stomach is by infusing the liquid into the stomach through the connection 14. For example, after eating a meal and drinking liquids, the subject may attach the device to the connection 14, and siphon out a large portion of the stomach contents (e.g., fluid with solid particulate, pieces, and/or chunks of food). For a typical meal, the volume of this initial siphoning operation may be on the order of 750 cc, but that number will of course vary based on the volume and characteristics of the ingested meal. Once the siphon effect stops, the subject infuses water back through the connection 14 into the stomach and then initiates another siphoning operation to remove the infused water, which will carry out additional solid food particles, pieces and/or chunks. The infusing and siphoning steps may then be repeated until the desired amount of ingested material is removed from the stomach. An example of a suitable volume for infusing into the stomach during the infusing step is 180 cc, although any other volume may be used.

Note that the methods described herein are preferably used to remove a significant portion of the food that the patient has ingested (e.g., between 30 and 60%, and more preferably between 40 and 50%, of the ingested food). Removing all the food that was ingested by the patient is not preferred and will usually be impractical. Examples of systems that implement both the removal of ingested material and the infusion of fluids are described below.

Figure 2:
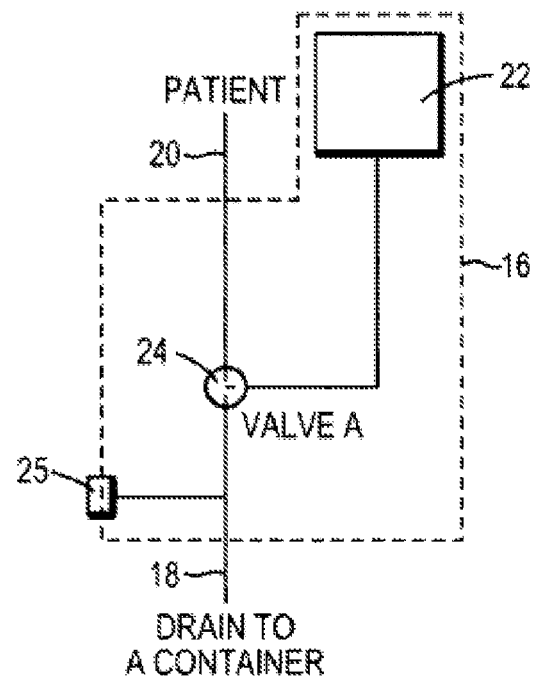
FIG. 2 is a schematic representation of a first embodiment for implementing the system shown in FIG. 1.

FIG. 2 schematically shows a first embodiment of a system for alternately removing ingested material from a stomach and infusing fluid into the stomach. The fluid may be any biocompatible fluid such as water or saline, and may optionally include one or more nutrients and/or medications. As shown, the assembly 16 includes a fluid source 22 and a valve arrangement 24 in communication with the fluid source 22, the drain line 18, and the patient line 20. The valve arrangement 24 may include one or more valves and any type of valve, such as, but not limited to, check valves, blade occluder and diverter valves. For example, the valve arrangement 24 may be implemented using a single 3-way valve with two operating positions—one position that opens a path between the patient line 20 and the drain line 18, and another position that opens a path between the fluid source 22 and the patient line 20. Alternatively, the valve arrangement 24 may be implemented using two valves—a first valve used to open a path between the patient line 20 and the drain line 18 and a second check valve used to open a path between the fluid source 22 and the patient line 20 when fluid is pumped from the fluid source 22 into the patient's stomach via connection 14 (shown in FIG. 1). In operation, the first valve is opened to drain the contents of the stomach. The first valve is then closed and fluid is pumped from the fluid source 22 to the patient line 20. Optionally, the first valve may be closed automatically by the fluid when the fluid is pumped from the fluid source 22. The first valve may then be re-opened to drain content of the stomach when fluid is no longer pumped to the patient line 20.

Figure 3:
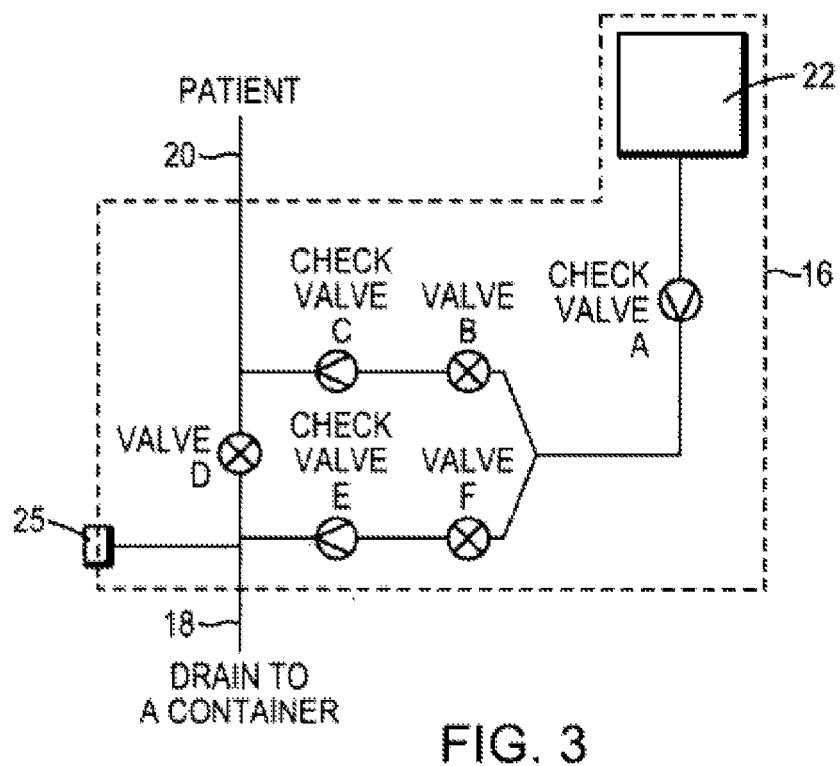
FIG. 3 is a schematic representation of a second embodiment for implementing the system shown in FIG. 1.

Other embodiments may include a plurality of valves, such as shown in FIG. 3. FIG. 3 schematically shows an assembly 16 having a check valve, valve A, in communication with the fluid source 22 and also with two valves, valve B and valve F. Valve B is in communication with a check valve, valve C, which is in communication with the connection 14 (shown in FIG. 1) via the patient line 20. Valve F is in communication with a check valve, valve E, which is in communication with the drain line 18. Another valve, valve D is in communication with the patient line 20 and the drain line 18. Valve B and valve F may be coupled, such that valve B is opened when valve F is closed, and valve F is opened when valve B is closed. In operation, valve B is opened while valve F is closed. Valve D may then be opened to drain the contents of the stomach received from the patient line 20. Optionally, the system may be configured so that as fluid is pumped through valve B and valve C, the movement of the fluid closes valve D and permits the fluid to flow into the stomach through the patient line 20. When fluid is no longer pumped through valves B and C, valve D may be activated automatically or manually to re-open to drain content of the stomach. When finished removing content from the stomach, valve D is closed and valve B is closed, which in turn opens valve F. The fluid may then be pumped through valve A, valve F and valve E to the drain line 18 in order to clean the drain line after use.

Variations on the assembly 16 shown in FIG. 3 may be implemented using one or more pumps in communication with the valve arrangement 24, the fluid source 22 and/or the drain line 18. For example, a pump may be coupled between the fluid source 22 and the patient line 20 with a check valve in communication with the fluid source 22 and the pump and another check valve in communication with the pump and the patient line 20 to facilitate fluid flow to the connection 14 (shown in FIG. 1). A pump may be coupled between the patient line 20 and the drain line 18 with a check valve in communication with the patient line 20 and the pump and another check valve in communication with the pump and the drain line 18. A pump may also be provided by the squeezing of a hand, e.g., squeezing the fluid source. A combination of two or more pumps may be used, to facilitate fluid flow to the patient line 20, to the drain line 18, or both. For example, during operation, if the system becomes clogged with content of the stomach such that the draining and/or infusing is not functioning properly, a pump may be provided to clear the obstruction in the patient line 20 and/or the drain line 18. Various types of pumps may also be used, such as, but not limited to, a diaphragm pump, a spring loaded piston pump, a syringe pump, a peristaltic pump, a flexible vein pump, a pneumatically actuated pump or a combination thereof. The pump(s) may be removable from the system such that a pump is only provided when necessary.

Referring now to FIGS. 2 and 3, a removable syringe may be provided at an auxiliary port 25 to provide suction for removing clogs from the patient line 20 and/or drain line 18. Although various configurations have been discussed for the valves and pumps with respect to FIGS. 2 and 3, it will be apparent to those skilled in the art that any number, kind, and/or configuration of valves and pumps may be used.

FIGS. 4 and 5A-5C show an embodiment of a system for removing ingested material from the stomach. In this embodiment, the system includes the fluid source 22, the drain line 18, and the patient line 20 and also includes an actuation handle 26 for opening and closing a path between the patient line 20 and the drain line 18 and for opening and closing a path between the fluid source 22 and the patient line 20. In operation, the actuation handle 26 may toggle the assembly 16 between two modes, a drain mode and an infusion mode. For example, in the drain mode, the actuation handle 26 may be in its original or un-actuated position which may cause the path between the patient line 20 and the drain line 18 to be opened and the path between the fluid source 22 and the patient line 20 to be closed, thus permitting content of the stomach to be drained. When the actuation handle 26 is squeezed or actuated, the actuation handle 26 causes the path between the patient line 20 and the drain line 18 to be closed and the path between the fluid source 22 and the patient line 20 to be opened. The actuation handle 26 causes the fluid source 22 to be squeezed or pumped, forcing the fluid out of the fluid source 22, thus allowing fluid to flow into the stomach in the infusion mode. For example, a user may squeeze the actuation handle 26 and fluid source 22 by hand. When the actuation handle 26 is released, the actuation handle 26 is returned to its original position, e.g., by a spring force, such as an extension spring, causing the path between the patient line 20 and the drain line 18 to be re-opened and the path between the fluid source 22 and the patient line 20 to be re-closed. The actuation handle 26 may cause the various paths to be opened or closed using any of a variety of approaches that will be apparent to persons skilled in the relevant arts, e.g. by pressing or pinching the various fluid lines or actuating valves.

Still referring to FIGS. 4 and 5A-5C, the system may also include a patient line cap 28 and a patient port plug 30 for when the system is not in use and removed from the patient. For example, the assembly 16 may be removed from the patient line 20 and the patient line cap 28 may be used to terminate the patient line 20. Similarly, the patient port plug 30 may be used to plug the opening where the patient line 20 couples to the assembly 16.

The assembly 16 may also include a rinse slide 32 for opening and closing a path between the fluid source 22 and the drain line 18. After the system is used to infuse fluid into the stomach and drain contents out of the stomach, the fluid source 22 may be used to rinse out or clean the patient line 20, the drain line 18 or both. Upon completion of use, the actuation handle 26 may be squeezed with the fluid source 22 to cause fluid to flow through and clean the patient line 20. Once the patient line 20 is clear, the patient line 20 may be clamped while still holding the actuation handle 26 and the patient line 20 may be disconnected from the assembly 16. The actuation handle 26 may then be released. In order to clean the drain line 18, the rinse slide 32 may be activated, allowing fluid to flow from the fluid source 22 down the drain line. When the rinse slide is activated, both valves open and since the drain line is lower than the fluid source, the fluid flows out of the drain line 18. The actuation handle 26 may then be squeezed with the fluid source 22, causing fluid to be pumped out of the fluid source 22 and through the drain line 18, cleaning the drain line 18.

Figure 4:
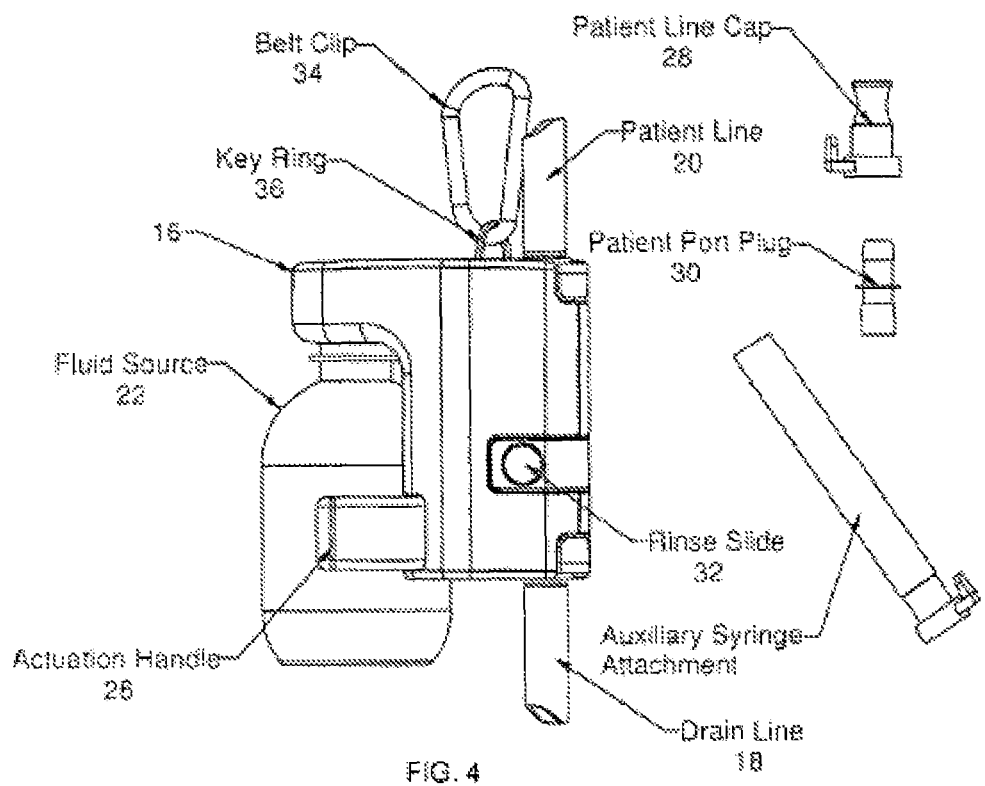
FIG. 4 shows a side view of a third embodiment for implementing the system depicted in FIG. 1.
Figure 5A:
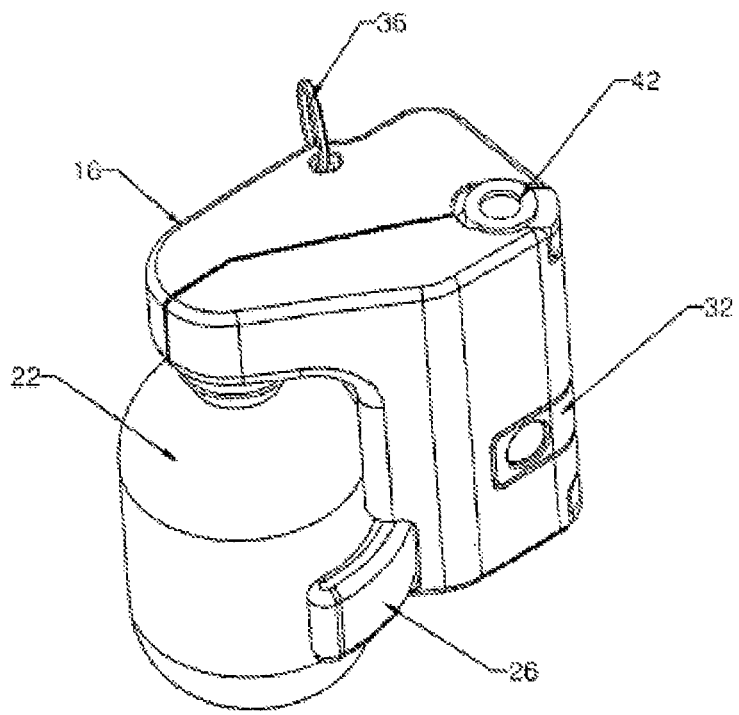
FIG. 5A shows an isometric view of the FIG. 4 embodiment.
Figure 5B:
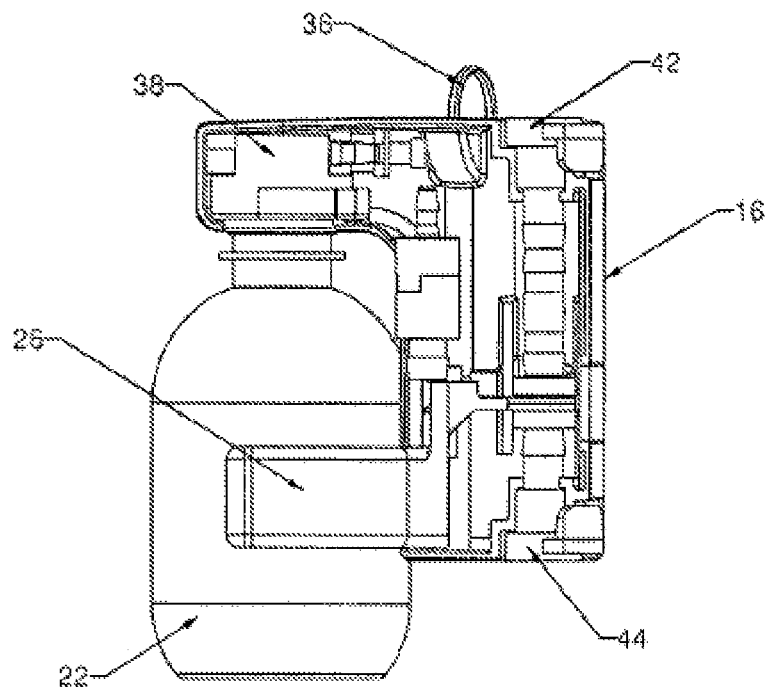
FIG. 5B shows a front view of internal components of the FIG. 4 embodiment.
Figure 5C:
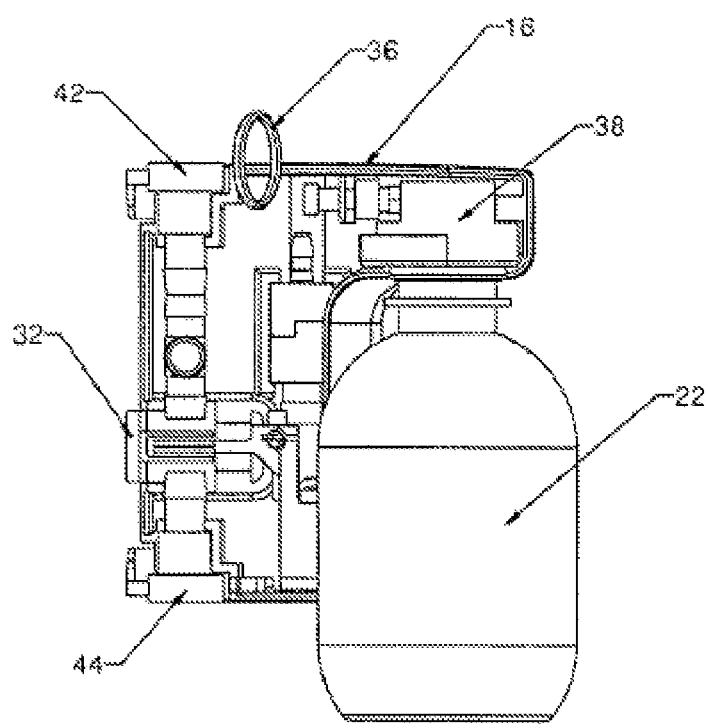
FIG. 5C shows a back view of internal components of the FIG. 4 embodiment.

Referring now to FIG. 4, optionally, the system may include an attachment mechanism 34 such as a belt clip, for attaching the assembly 16 to the patient during use of the system. Now referring to FIGS. 4 and 5A-5C, the attachment mechanism 34 may be coupled to the assembly 16 at an attachment location 36. The fluid source 22 may be coupled to the assembly 16 at an attachment assembly 38.

Figure 6A:
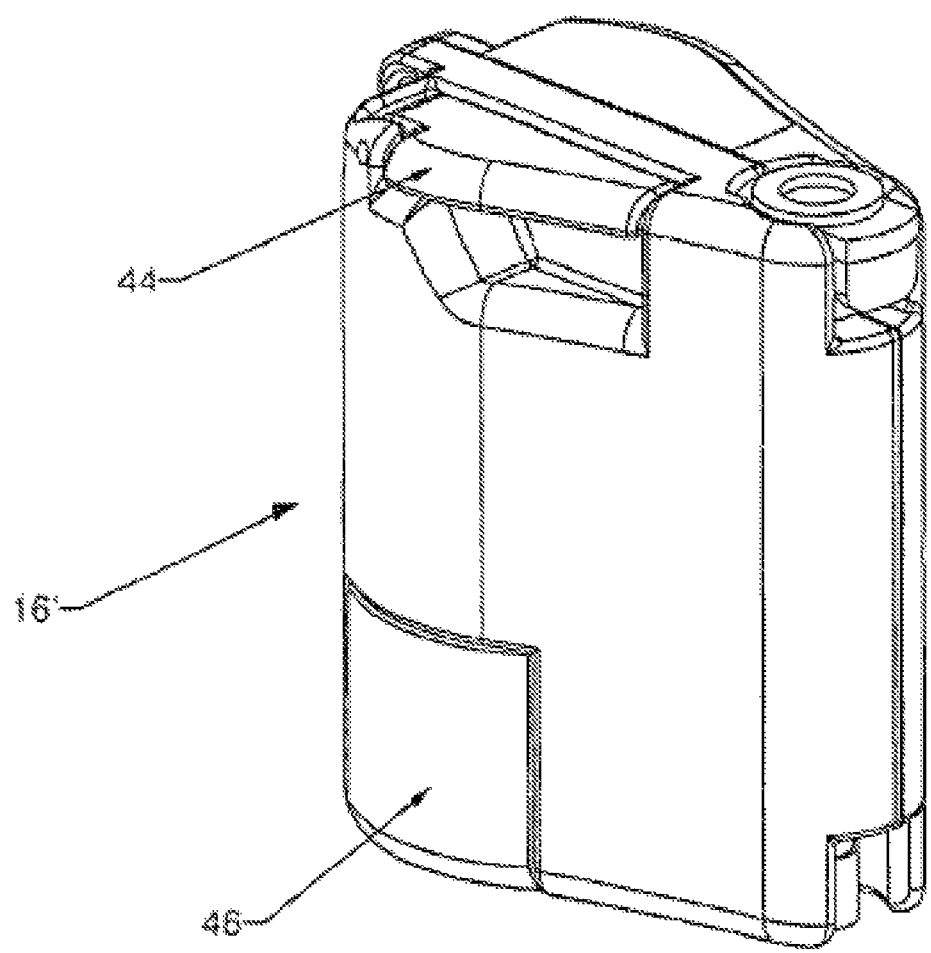
FIG. 6A shows an isometric view of another embodiment for implementing the system depicted in FIG. 1.
Figure 6B:
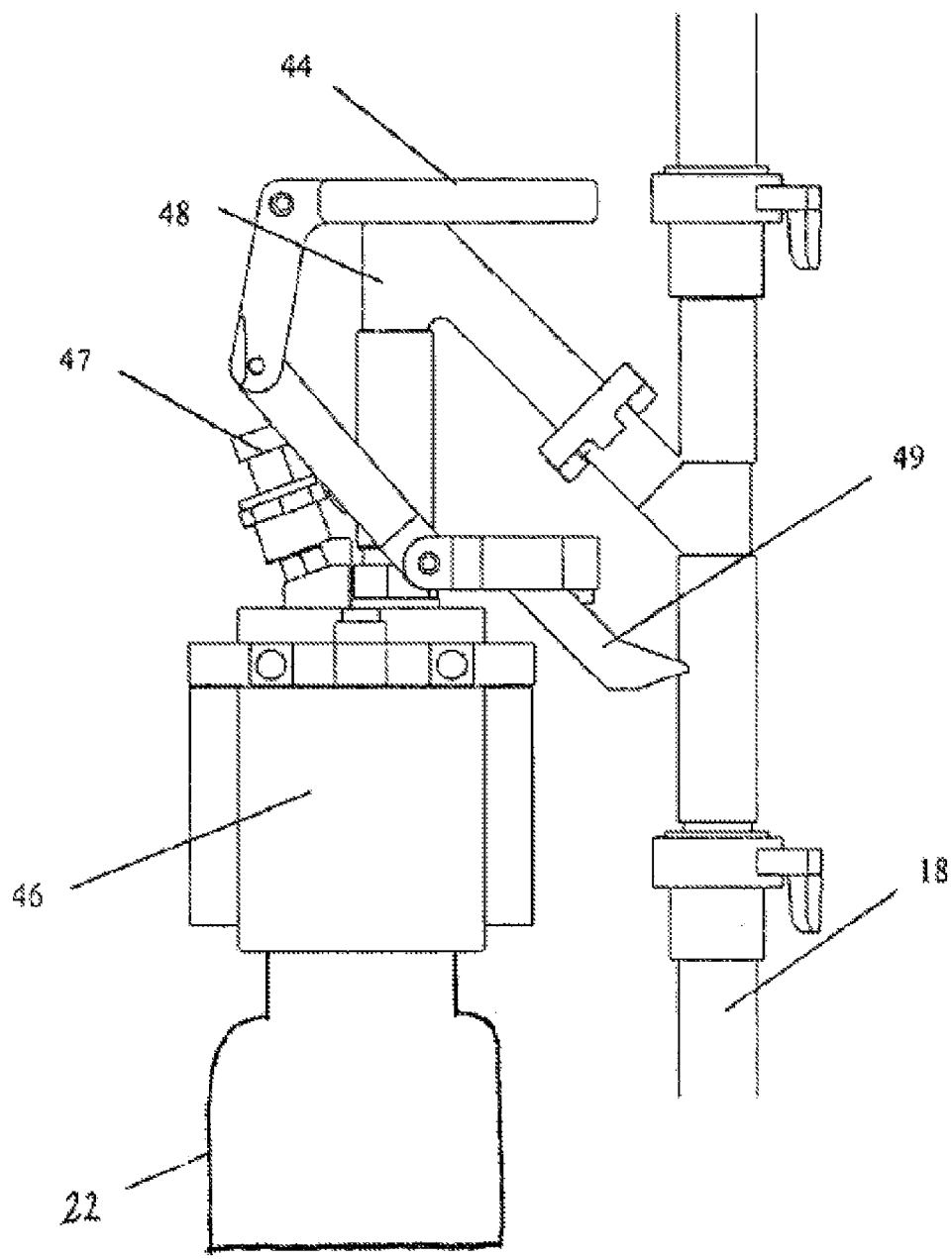
FIG. 6B shows a front view of internal components of the FIG. 6A embodiment.

FIGS. 6A and 6B depict an alternative assembly 16' that may be used in place of the assembly 16 depicted in FIGS. 4 and 5A-5C. In this embodiment an actuation lever 44 alternately either (a) opens a path between the patient line 20 and the drain line 18 or (b) closes the path between the patient line and the drain line. Referring now to FIG. 6B, when the lever 44 is actuated in this embodiment, it causes the path between the patient line 20 and the drain line 18 to be clamped by clamp 49 and the path between the fluid source 22 and the patient line 20 to be opened. When the fluid source 22 is squeezed while the lever 44 is in an actuated position, fluid from the fluid source 22 will flow through a check valve, into the patient line and into the stomach. When the lever 44 is in a non-actuated position, the path between the patient line 20 and drain line 18 is open. Upon squeezing the fluid source 22 in a non-actuated position, water flows from the fluid source 22 through the drain line 18 and causes a rinsing effect, which obviates the need for the separate rinse slide. In the illustrated embodiment, the actuation lever 44 may cause the paths to be closed/opened by clamp 49 pressing or pinching on the tubing lines. However, persons skilled in the relevant arts will recognize that alternative approaches for opening and closing the various fluid flow paths may be substituted by making appropriate modifications.

Since water bottles may have varied thread designs which would not ordinarily mate with conventional female fittings, a universal fluid source receptacle 46 may optionally be implemented to accept any water bottle neck, and to lock around the bottle neck flange. Upon actuation the receptacle releases the flange on the fluid source. This feature may also be implemented in the other embodiments described herein.

The system is preferably connected to a gastrostomy tube that has previously been installed in a patient (e.g., through the patient's abdominal wall), with a port that extends out of the patient's body. Preferably, the port is relatively flush with the surface of the patient's abdomen and has a connector that mates with a mating connector of the system. A variety of ways to implement such a flush mount connection interface can be readily envisioned.

FIGS. 8-15 depict one preferred implementation of a flush mount connection interface. One part of the interface is the "skin connector" 60 (shown in FIGS. 9-12) which is an implementation of the connection 14 discussed above in connection with FIG. 1, and is affixed to the patient and the gastrostomy tube 45 that resides inside the patient's stomach. This embodiment of the skin connecter 60 includes a rotational valve assembly that controls opening and closing of the pathway into the stomach, as shown in FIGS. 14A-14B. The other part of the interface is the "tube connector" 65, also shown in FIGS. 14A-14B, which is positioned at the upper end of the patient line 20 and is designed to mate with the skin-connector 60 with a fluid-tight interface.

Figure 12A:
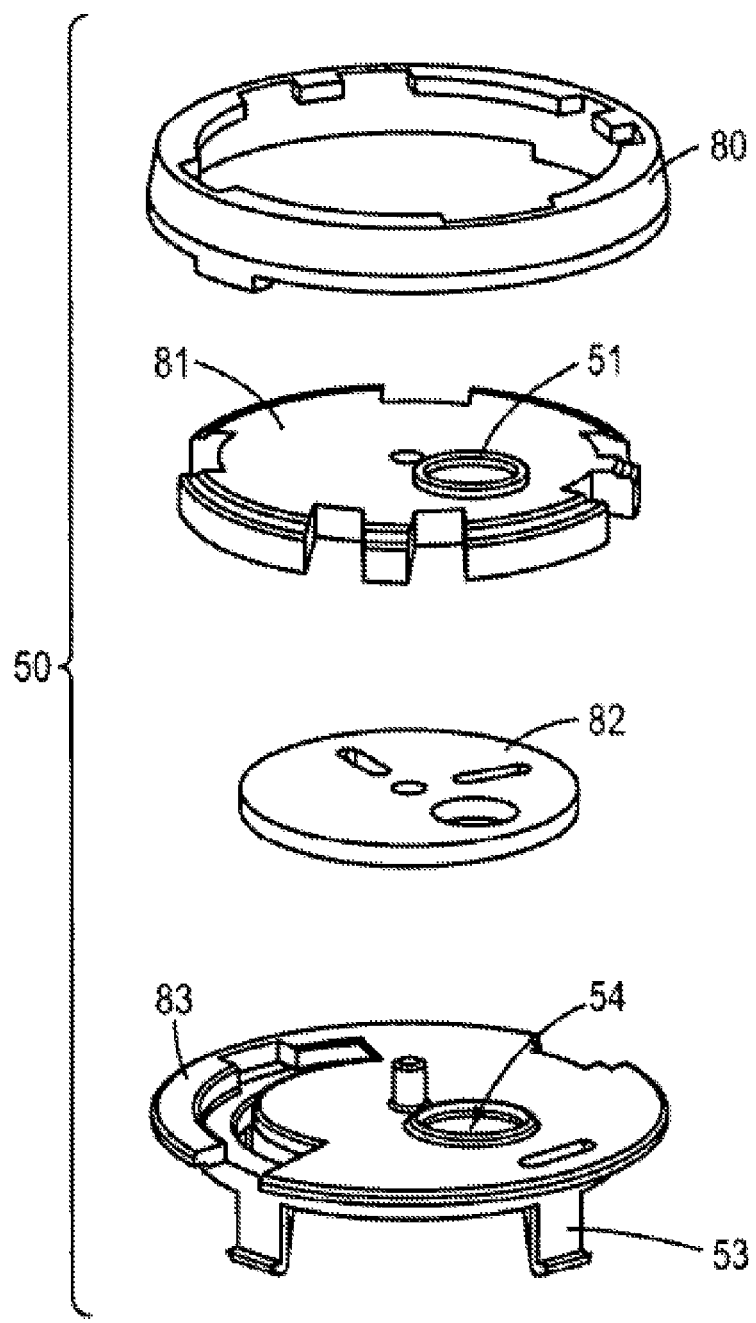
FIG. 12A is an exploded view of the rotational valve assembly for the embodiment shown in FIGS. 8A-8C.

FIGS. 9-11 depict a rotational valve assembly 50 that is assembled inside a skin flange 55 to create a flush mount skin connector 60, and FIG. 12A is an exploded view of the rotational valve assembly 50. Three of the valve assembly components 81, 82, 83 have a thru-hole biased to one quadrant, arranged so that the valve is opened when the thru-holes are aligned and so that the valve is closed when the thru-holes are not aligned. In the preferred embodiment, the size for the entire valve assembly ranges from about 3 cm to about 4 cm in diameter, and the size for the thru-holes is about 6-8 mm in diameter. In the valve assembly 50 the platform diameter can measure from about 3.5 to about 7 times larger than the diameter of the thru-hole that passes therethrough. However, in other embodiments, the valve assembly can be proportionally different size, either larger or smaller. The valve assembly 50 is preferably constructed of top platform 81 and a bottom platform 83, with a layer of elastomer 82 that is attached to the top platform 81 and sandwiched between the top platform and the bottom platform 83 with a force that is high enough to prevent leaks, yet low enough to permit rotation of the elastomer 82 with respect to the bottom platform 83. The elastomer is attached to the top platform using any adhesive that would attach the silicon to the plastic, however, in one embodiment, a primer and a fast curing adhesive is used. The top platform 81 is preferably made of a lubricious plastic for example, acetyl, and in some embodiments, DELRIN®, TEFLON®, polyethylene, etc, can be used, and the bottom platform 83 is preferably made of ABS or another hard plastic that is, for example, biocompatable. However, in alternative embodiments, those components may be made of other materials that provide similar functionality. In some embodiments, the first platform is placed adjacent to the patient's skin. The first platform can be mounted adjacent the patient's skin. In some embodiments, the first platform can directly contact and sit against the patient's skin. A top retaining ring 80 is configured to attach to the bottom platform 83 to retain the top platform 81 and the middle layer 82 while allowing those two layers to rotate with respect to the bottom platform 83. Attaching can be in the form of snap fitting, welding, gluing or any other method of attachment. The top retaining ring 80 is preferably also made of ABS or another hard plastic.

In some embodiments, the components of the valve assembly (e.g., the top platform and the bottom platform) move with respect to one another. As discussed, one platform can move with respect to another platform by a rotational force. However, thru-holes that pass through each of these platforms can move with respect to one another by other suitable forces by, for example, a force in a linear direction. The geometric shape of the components of the valve assembly may be adjusted to enable alternative forms of movement, for example, the platform, a retainer, and/or the elastomer layer may have a square, rectangular or other suitable geometry the enables the thru-holes that pass through each platform (and optionally the elastomer layer) to alternately align and offset from one another. In such configurations, one platform may be moved linearly backward and forward with respect to the other platform (i.e., move linearly backward to provide the first position and move linearly forward to provide the second position) or the movement can be in a single direction, for example.

In the illustrated embodiment, as best seen in FIGS. 9-11, the valve assembly 50 has protrusions 53 at its bottom that allows it to fasten to recesses 56 in the skin flange 55 to form the skin connector 60. The top face of the valve assembly preferably has a structure (e.g., the top platform 81 has the cut-outs 52) for mating with a corresponding surface on the tube connector 65. The valve assembly 50 can be disassembled from the skin connector 60 by pushing the protrusions 53 at its bottom out of the recesses 56 in the skin flange 55. With significant force, manually or with a tool directed at the bottom of the recesses 56, the barbed protrusions 53 can be freed from the recesses 56 in skin flange 55 and the valve assembly 50 can be removed.

Removal of the valve assembly 50 from the skin connector 60 may be required when a course of treatment is finished or in connection with valve replacement due to wear, scheduled maintenance, cleanliness, or length adjustment. Using a removable valve permits adjustment of the length of the gastrostomy tube (e.g. after patient weight loss) to compensate for a shortened stoma tract. After the valve assembly 50 is removed, the tube is cut to a shorter length, and then the valve is replaced, advantageously avoiding the need to replace the gastrostomy tube.

In some embodiments, the valve assembly 50 is connected directly to the gastrostomy tube such that its bottom platform 83 sits against the patient's skin. In this way, use of the skin flange 55 is avoided. Optionally, the bottom platform 83 has a smooth surface and does not contain protrusions.

In some embodiments, an assembly includes a valve and a tube having a first fluid pathway for disposal in a body of a patient. The valve has a bottom platform, a top platform and a retainer. The bottom platform and the top platform each has a thru-hole that passes therethrough. A retainer retains the bottom platform in proximity to the top platform so that the top platform can be moved with respect to the bottom platform between a first open position that aligns the thru-holes of the bottom and top platforms and a second closed position that offsets the thru-holes of the bottom and top platforms. The proximal end of the tube disposed in a patient's body is mated with the thru-hole in the bottom platform. A second tube that is external to the patient's body has a second fluid pathway. The second fluid pathway can supply water or other fluid to the assembly. A distal end of the second tube is adjacent the thru-hole in the top platform. The first fluid pathway and the second fluid pathway join to form a single fluid pathway. When the valve is positioned in the first position, the open position, the two thru-holes align to provide access through the single fluid pathway. In the second position, the closed position, the thru-holes offset to provide a fluid tight seal and to prevent access through the fluid pathway. In some embodiments, each of the tube in the patient's body, the two thru-holes, and the external tube has a substantially similar internal diameter, thus the flow of fluid through this single fluid pathway is substantially consistent, i.e., it is not restricted by a changing internal diameter. In some embodiments, the top platform is moved in a substantially linear direction with respect to the bottom platform. In some embodiments, placement of the valve in the second position, the closed position, offsets the thru-holes to provide a fluid tight seal and to prevent access through the fluid pathway when the external tube is disconnected from the tube in the patient's body. In some embodiments, in order to disconnect the external tube from the valve the valve must first be positioned in the second position, the closed position.

Due to protrusions 66 on the contacting surface of the tube connector 65 being configured to mate and mechanically couple with the cut-outs 52 on the valve assembly 50 at a rotational distance of approximately 120° from the "open" position of valve assembly 50, fluid will not leak out of valve assembly 50 during tube connector 65 removal (i.e. disc 68 is always covering the passageway of skin connector 60 prior to removal.)

For a gastrostomy tube designed to aspirate food from a full stomach (i.e. larger diameter to accommodate food particles,) the fluid pressure may be higher than traditional feeding tubes, and the illustrated valve embodiments can withstand such higher pressures without leaking. The illustrated valve embodiments are also designed to provide a large, uniform lumen from the tube through the valve. The rotational gasket configuration allows sealing of the tube without restricting the lumen dimension when the valve is in the "open" position, thereby minimizing the probability of tube clogging during food aspiration.

Figure 12B:
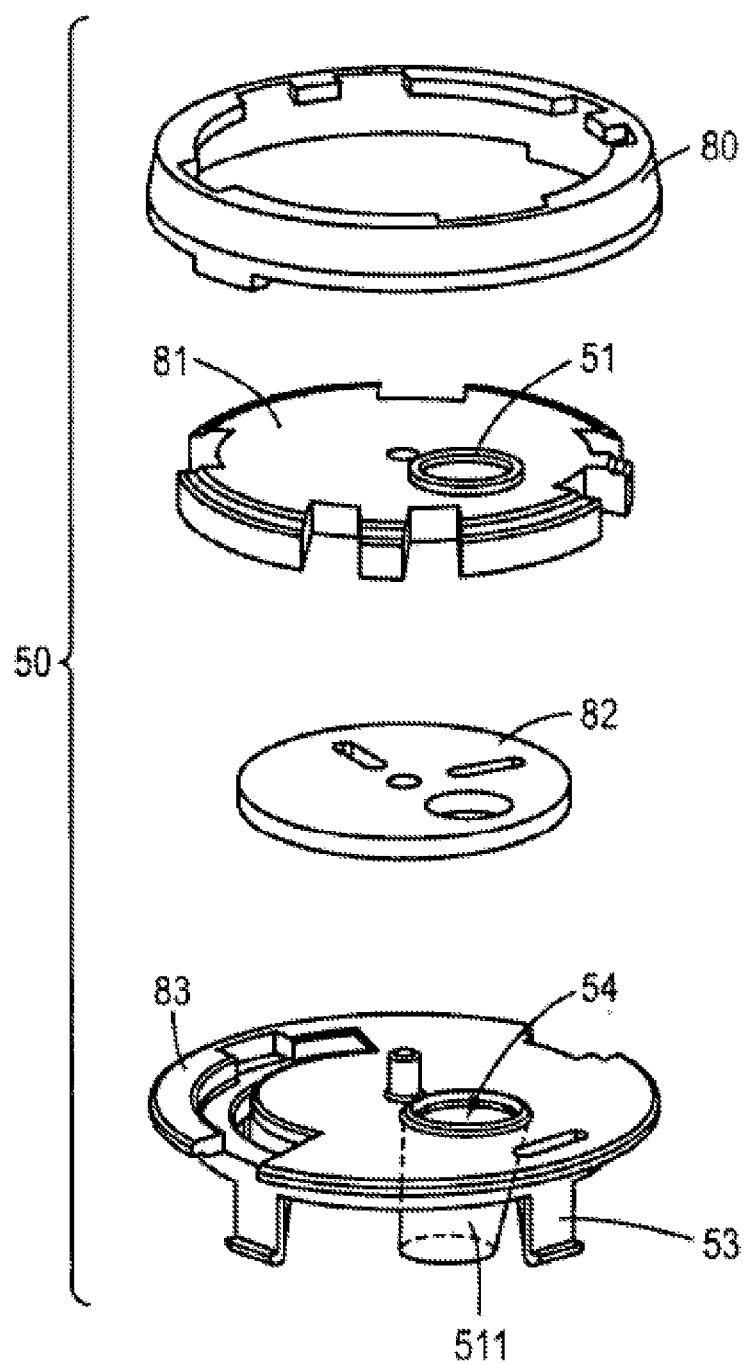
FIG. 12B is an exploded view of another embodiment of the rotational valve assembly for the embodiment shown in FIGS. 8A-8C.

In one embodiment, referring to FIGS. 11-12, the skin connector 60 skin flange 55 has a thru-hole 57. The thru-hole 57 can be shaped to complement the gastrostomy tube when an end of the gastrostomy tube is interested in the thru-hole 57. The bottom platform 83 can include spout 511 (FIG. 12B) that, for example, surrounds the thru-hole 54. The spout 511 of the thru-hole 54 can be sized to enter the lumen of the gastrostomy tube. For example, an end of the gastrostomy tube is positioned so that the spout 511 of the thru-hole 54 enters its lumen and a portion of the gastrostomy tube is compressed between the spout 511 and the thru-hole 57 of the skin flange 55. The thru-hole 57 of the skin flange 55 can be shaped to improve compression of the gastrostomy tube, for example, the thru-hole 57 can have a funnel shape. In one embodiment, the outer diameter of the spout 511 is the same as the inner diameter of the proximal end of the gastrostomy tube. The shape of the thru-hole 57 can be selected according to the shape of the spout 511 surrounding the thru-hole 54 of the bottom platform 83. Compression of the spout 511 against the thru-hole 57 can create a water-tight seal. In one embodiment, at least a portion of the gastrostomy tube is made from a hydrophobic gasket material such as, for example, ePTFE. The portion of the gastrostomy tube containing a hydrophobic gasket material may be compressed between the spout 511 and the thru-hole 57 thereby forming a water-tight seal that prevents leakage of the gastrostomy tube. In another embodiment, the thru-hole 57 defined by the flange 55 has an inside surface with a thread that complements a helical support structure disposed on at least a portion of an outside surface of the gastrostomy tube. Support for a gastrostomy tube having a helical support structure and/or employing ePTFE my be found in U.S. patent application Ser. No. 11/824,953 entitled "Shunt Apparatus for Treating Obesity by Extracting Food" by Solovay et al., which is incorporated by reference. In embodiments where the skin connector 60 includes a spout 511 surrounding the thru-hole of the bottom platform 83 and/or the flange has an inside surface with a thread the complements a helical support structure on the gastrostomy tube, removal of the valve required when treatment is finished or in connection with valve replacement can require additional steps. For example, prior to or after unfastening protrusions of the valve 50 from the flange 55 the spout 511 is removed from the lumen of at the proximal end of the gastrostomy tube. In another example, prior to or after unfastening protrusions of the valve 50 from the flange 55 the valve 50 is rotated in a direction opposite the helical support disposed on the gastrostomy tube thereby to remove the valve 50 from the gastrostomy tube.

Referring to FIGS. 11-13, in one embodiment, a proximal end of a gastrostomy tube is mated with a thru-hole in the bottom platform of a skin connector 60. The bottom platform 83 is placed adjacent to the patient's skin, optionally, a portion of the skin connector's 60 flange 55 is between the bottom platform 83 and the patient's skin. The skin connector 60 can be placed adjacent to the patient's skin. The skin connector 60 is rotated to a first position to cause the thru-hole 51 that passes through the top platform 81 to substantially align with the thru-hole 54 in the open position to provide access to the fluid pathway for a first period of time. When the skin connector 60 is in the first position, the patient's stomach contents can be aspirated through the gastrostomy tube. Rotating the skin connector 60 to the first position avoids restriction of the gastrostomy tube thereby aiding aspiration. The skin connector 60 is rotated to a second position to cause the thru-hole 51 to be offset from the thru-hole 54 to provide a fluid tight seal to the proximal end of the gastrostomy tube and to prevent access to the fluid pathway for a second period of time.

In some embodiments, a proximal end of a tube other than a gastrostomy tube is mated with a thru-hole 54 in the bottom platform 83 and the bottom platform 83 is placed adjacent to the patient's skin. Providing the valve 50 in the first position provides access to a fluid pathway in the tube during a first period of time and providing the valve 50 in the second position provides a fluid tight seal to the proximal end of the tube and access to the tube's fluid pathway is prevented during a second period of time.

Figure 13A:
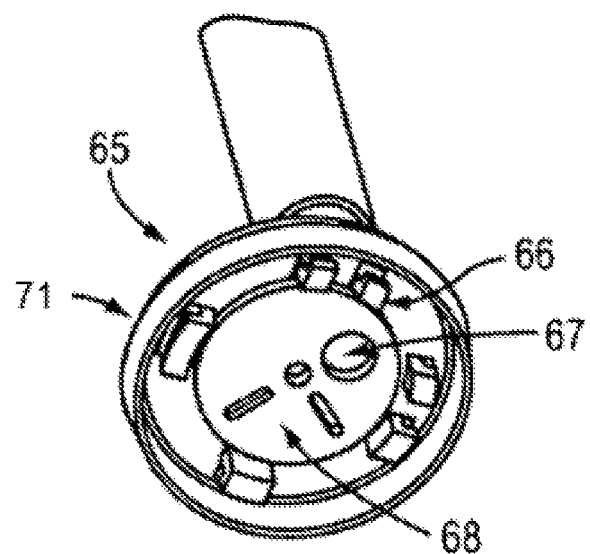
FIG. 13A shows a bottom view of a tube connector assembly for the embodiment shown in FIGS. 8A-8C.
Figure 13B:
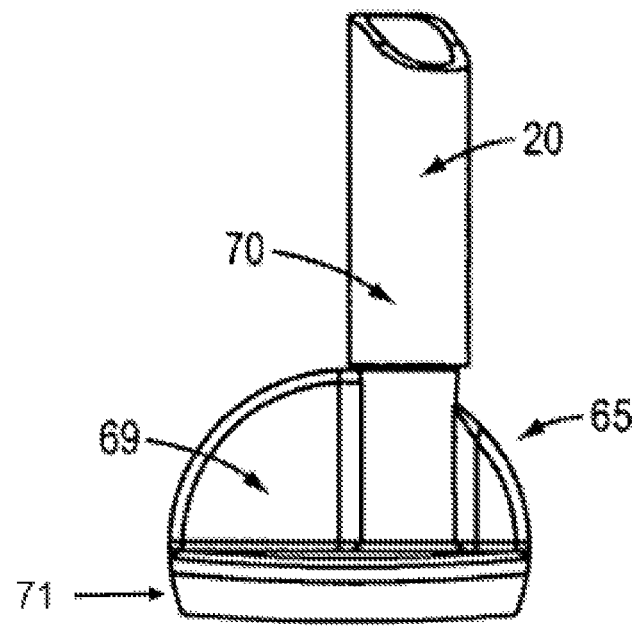
FIG. 13B shows a side view of a tube connector assembly for the embodiment shown in FIGS. 8A-8C.
Figure 14A:
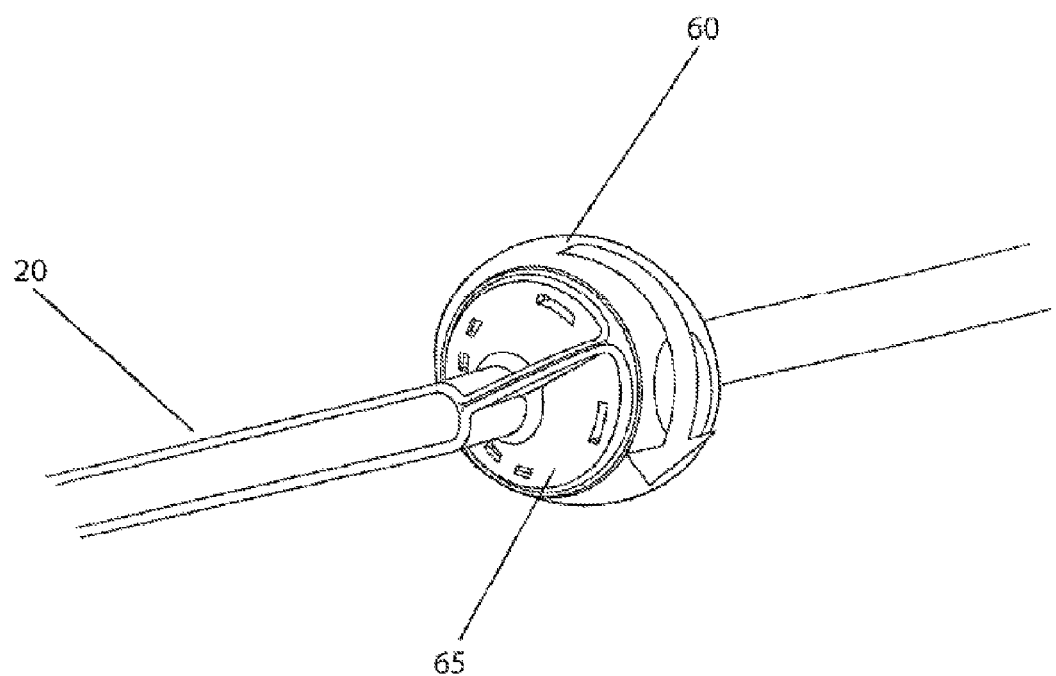
FIGS. 14A and 14B show the tube connector connected to the skin connector of the embodiment shown in FIGS. 8A-8C, in the closed and opened positions, respectively.
Figure 14B:
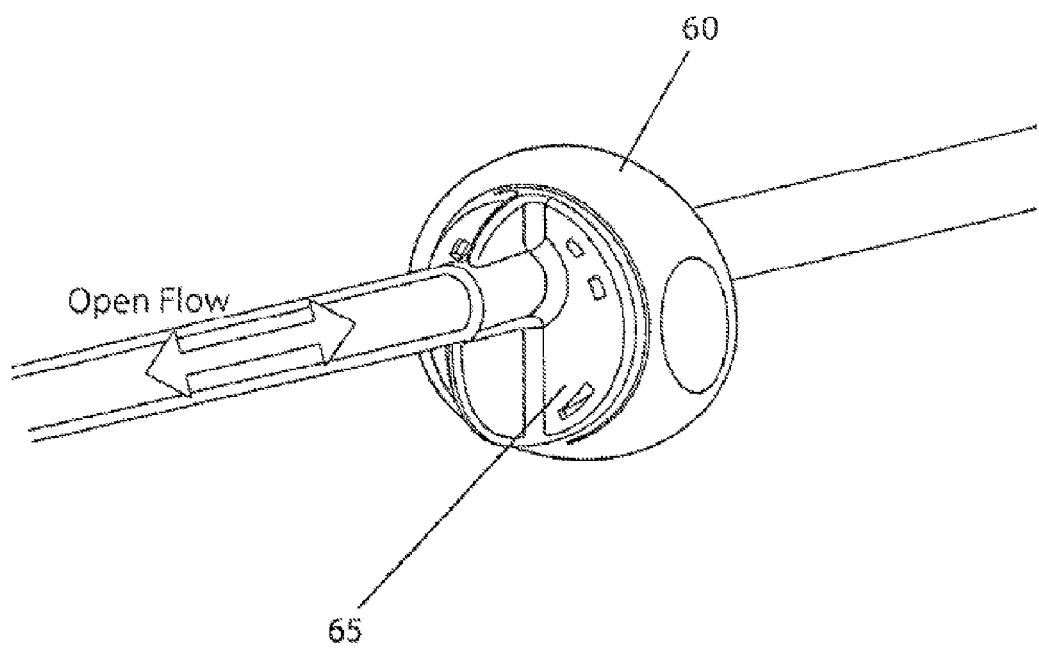
Figure 15:
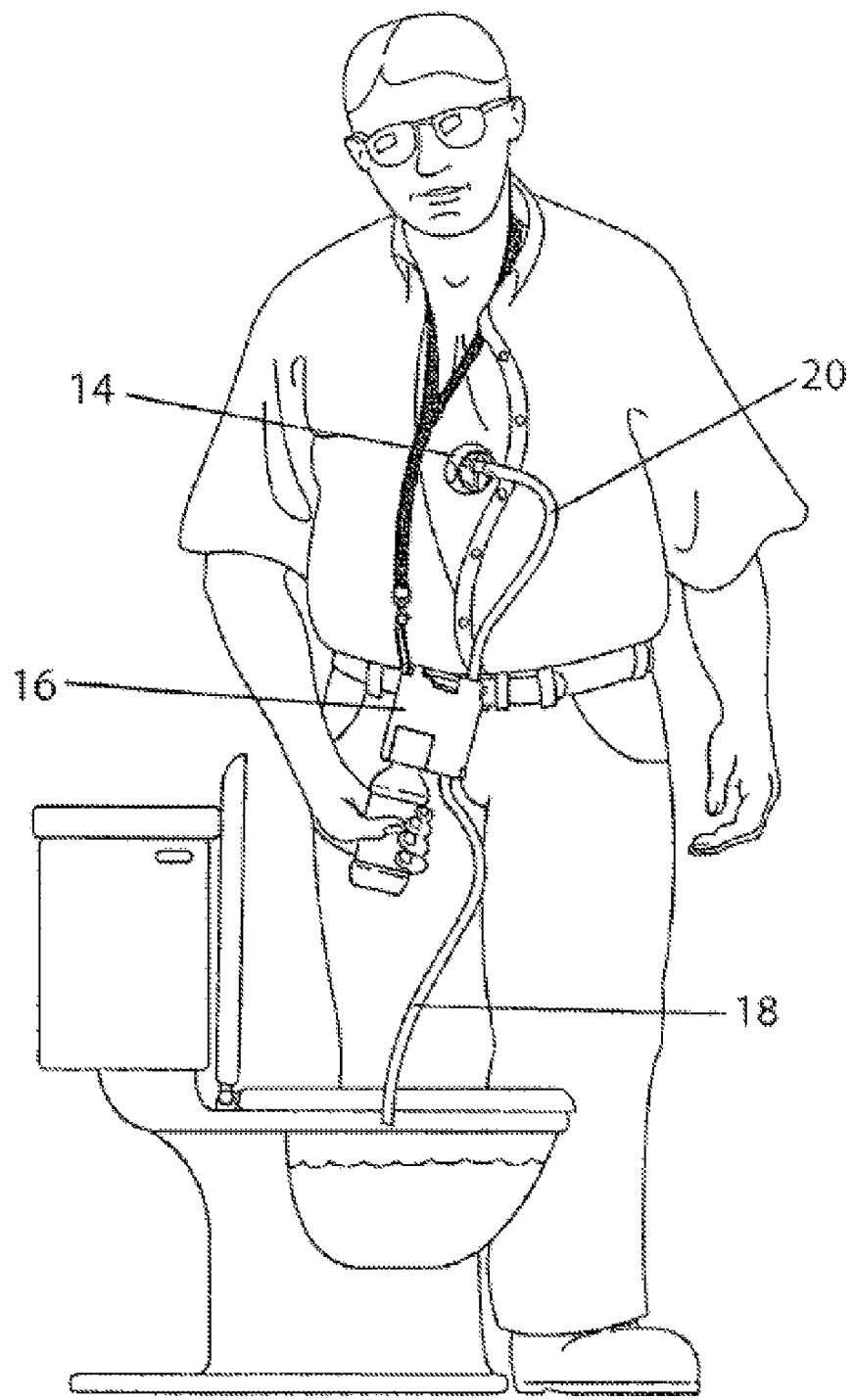
FIG. 15 shows the embodiment shown in FIGS. 8A-8C being used by a patient.

FIGS. 13A and 13B depict a tube connector 65 that is connected at the upper end of the patient line 20. The tube connector 65 is designed to mate with the skin connector, and protrusions 66 on the contacting surface of the tube connector 65 are configured to mate with the cut-outs 52 on the valve assembly 50 (both shown in FIG. 9B). The body of the tube connector 65 is preferably constructed of a hard plastic such as ABS. The contacting surface of the tube connector 65 is preferably implemented using a disc 68 made of an elastomeric material such as silicone, with a biased thru-hole 67 that is dimensioned and positioned to match the thru-hole of the skin connector. In the illustrated embodiment, the tube connector 65 has a ridge 71 around the perimeter of its contacting surface that is configured to fit into a mating surface of the skin connector (i.e., the valley 61 around the perimeter of the skin connector 60, shown in FIG. 10C). The outer surface of the illustrated tube connector also has a handle 69 for grasping by the user and a barbed hollow protrusion 70 that is in fluid communication with the thru-hole on the contacting surface for fastening to the patient line tubing.

Referring now to FIGS. 10C and 12-14, when the tube connector 65 and the skin connector 60 are not mated, the valve assembly 50 on the skin connector 60 is in a "closed" position, with the thru-hole 51 in the top platform 81 and the middle layer 82 oriented out of phase with respect to the thru-hole 54 in the bottom platform 83. To connect the tube connector 65 and the skin connector 60, the thru-hole 67 of the tube connector is aligned with the thru-hole 51 in the top platform 81 of the valve assembly 50. The tube connector 65 is then turned by grasping the handle 69 and turning it clockwise. When this happens, the biased thru-hole 51 in the top platform 81 and the middle layer 82 and the thru-hole 67 in the tube connector 65 will all rotate together into alignment with the thru-hole 54 in the bottom platform 83 of the valve assembly 50, thereby opening a passage to the gastrostomy tube. Rotating the tube connector 65 clockwise also engages mating features 66 on the tube connector with corresponding cut-outs 52 on the valve assembly 50 (shown in FIG. 9B) to lock the tube connector 65 to the skin connector 60. The fluid pathway of the patient line 20 of the tube connector 65 can join with the fluid pathway of the gastrostomy tube 45 that connects to the skin connector 60 thereby providing a single fluid pathway.

After the passage is open, removal of ingested material from the patient's stomach is performed, as described above (optionally in alternation with the infusing of liquids into the patient's stomach). Subsequently, the patient or practitioner rotates the tube connector 65 counterclockwise, which causes the thru-hole 67, the biased thru-hole 51 in the top platform 81, and the middle layer 82 to all rotate together away from the thru-hole 54 in the bottom platform 83 of the valve assembly 50, to the position shown in FIG. 14A, thereby closing the valve in the skin connector 60. The tube connector 65 can then be pulled away from the skin connector 60.

Referring now to FIGS. 10-11, the skin connector 60 is preferably constructed with an outer skirt 58 composed of a soft, compliant material (e.g. elastomer, foam, etc.) that tapers the fully assembled low-profile skin-port towards the skin to provide a more aesthetic appearance, to prevent the skin connector 60 from catching on the user's clothing, and to serve as a bumper against applied stresses. In alternative embodiments, the skin connector 60 and tube connector 65 can be configured in various other forms and/or can use different materials to optimize various characteristics. For example, both the skin connector 60 and tube connector 65 can be made with an oblong shape. More specifically, one or more of the top platform, the bottom platform, the disk, and the retaining ring (i.e., the retainer) have an oblong shape. The mating features and turning of the valve can be actuated by alternate means that will be apparent to persons skilled in the relevant arts, including but not limited to thumbwheel mechanisms, scissor mechanisms, etc. When mounted on the surface of the patient's skin, the skin connector 60 and/or the combination of the skin connector 60 mated to the tube connector 65 sits above the patient's skin at a distance that measures from about 5 mm to about 20 mm, or from about 7 mm to about 9 mm. Thus, the overall height of the skin connector 60 and/or the combination of the skin connector mated to the tube connector 65 ranges from about 5 mm to about 20 mm, or from about 7 mm to about 9 mm. It is desirable for the skin connector 60 and/or the skin connector 60 mated to the tube connector 65 to have a low-profile (i.e., a small distance that measures from the patient's skin). Having a low-profile enables a patient to discretely wear the valve and discretely use the system to remove ingested material from the patient's stomach One potential side-effect of aspirating food from the stomach is lowering of electrolytes, such as potassium. The removal of hydrochloric acid (HCl) from the stomach along with food particles can cause the human body to excrete potassium to maintain a charge balance, and excretion of too much potassium can cause hypokalemia. One method for preventing hypokalemia is to give the patient potassium supplements and a proton pump inhibitor.

Another method for preventing hypokalemia is to selectively remove HCl from the extracted material, and return it to the patient's stomach, in order to prevent electrolyte imbalance and obviate the need for additional therapeutics. To achieve acid return to the stomach, the device may be configured with one or more semi-permeable filters that selectively screen out waste product and retain HCl for return to the stomach. Examples of suitable filters include mechanical filters, chemical filters, ionic membranes (e.g. anionic exchange membrane, cationic exchange membrane, bipolar membrane), and electrochemical filtrations systems (or a combination of the above).

One way to implement food evacuation with the return of acid to the stomach is by using two filters in series. The first filter, or pre-filter, separates food particles from the fluid. Examples of suitable filters for performing this function include mechanical filters like standard glass-fiber or cellulose filters that selectively remove solids above a specified particle size, leaving "waste" fluid. A suitable porosity for such a filter is 2.5 µm porosity. The second filter removes hydrochloric acid from the pre-filtered fluid. Examples of suitable filters for performing this function include semi-permeable membranes, or an anionic exchange membrane (e.g. NEOSEPTA™, Tokuyama, Japan).

FIG. 7A depicts a first embodiment for returning acid to the stomach. A siphon effect or a pump is used to force evacuated stomach contents through the pre-filter 110 and into one compartment 122 of a dual chamber container 120, which is separated from the other compartment 126 by an anionic exchange membrane 124. The second chamber 126 contains deionized water. The difference in ionic concentration between the dual chambers of the cell 120 will drive a diffusion dialysis process to occur in which the $Cl^-$ and $H^+$ ions from hydrochloric acid selectively transfer across the membrane 124 into the water filled chamber 126. The waste fluid can then be released to exit to the toilet, and a pump 130 can then be actuated to force the HCl and water solution back into the patient's stomach. FIG. 7B depicts an alternative embodiment that is similar to the FIG. 7A embodiment, but adds a separate water infusion subsystem 140 to allow the subject to continue to flush and siphon the stomach while the diffusion dialysis process is occurring. More complex filtration system can also be used, including but not limited to electrodialysis, or an anode and a cathode to separate charged ions in an electrophoresis like fluid suspension. The electrofiltration process could potentially decrease the time to remove the HCl from the waste product.

Repeated removal of food from a patient's stomach to achieve weight loss requires close medical supervision to avoid complications (e.g., a drop in electrolyte levels). It may therefore be desirable for the physician to ensure that the patient returns for follow-up and blood testing to avoid improper use of the device, or at a minimum have data that reveals the patient compliance with proper use of the system. A shut-off mechanism may be built into the system to ensure that the patient returns for such follow-up. The shut-off mechanism preferably operates based on some measurement of usage such as the passage of time (e.g., to disable the device after one month), the number of cycles of use (e.g., to disable the device after 90 uses), or the volume of extracted matter (e.g., to disable the device after 50 liters of material have been removed).

The measurement of usage may be implemented by mechanical or electrical means, as will be appreciated by persons skilled in the relevant arts (e.g., using a mechanical counter such as a multi-decade geared mechanism that is incremented using a cam-actuated sprocket, or an electrical counter that is incremented by a suitable sensor). Suitable events that can be used to increment the count include, but are not limited to, the connection of a water bottle to the system, the connection of the tube connector to the skin connector, etc. The shut-off mechanism may also be implemented by mechanical or electrical means. One example of a suitable mechanical shut-off mechanism is a preloaded spring mechanism that, when actuated, blocks fluid from moving through one of the system's tubes. An example of a suitable electrical device for implementing shut-off is a solenoid actuated valve, and a wide variety of alternatives will be apparent to persons skilled in the relevant arts. The shut-off mechanism may be designed to permanently disable the device, in which case the patient would have to obtain a new device to continue using the system. Alternatively, it may be configured to be resettable by a doctor (e.g., using an electronic shut-off mechanism that can be reset by entry of a password or a biometric key such as a fingerprint detector). After the patient is examined by the doctor (e.g., using blood tests to confirm healthy electrolyte levels), the doctor could provide a new device or reset the shut-off mechanism.

One application of some of the above-described embodiments is to implement a method of removing ingested food from a patient's stomach via a gastrostomy tube that passes through the patient's abdominal wall into the patient's stomach. This method includes the steps of: (a) siphoning a first portion of the ingested food out of the patient's stomach via the gastrostomy tube; (b) infusing liquid into the patient's stomach via the gastrostomy tube; and (c) siphoning at least some of the infused liquid out of the patient's stomach via the gastrostomy tube, together with a second portion of the ingested food. Optionally, this method may further include the steps of: (d) infusing liquid into the patient's stomach via the gastrostomy tube; and (e) siphoning at least some of the infused liquid out of the patient's stomach via the gastrostomy tube, together with a third portion of the ingested food, wherein step (d) is performed after step (c), and wherein step (e) is performed after step (d).

Another application of some of the above-described embodiments is to implement an apparatus for removing food from a patient's stomach via a gastrostomy tube that passes through the patient's abdominal wall into the patient's stomach. This apparatus includes: a connector configured to connect to a proximal end of the gastrostomy tube with a fluid-tight connection; a first fluid path provided between the connector and a drain port, configured to permit siphoning or pumping food from the patient's stomach out to the drain port; a second fluid path provided between the connector and an input port, configured to permit infusion of liquid from the input port into the patient's stomach; and a fluid circuit configured to alternately (a) open the first fluid path during a first interval of time to permit siphoning or pumping food out of the patient's stomach and (b) open the second fluid path during a second interval of time to permit infusion of the liquid in the reservoir into the patient's stomach.

Another application of some of the above-described embodiments is to implement a method of removing ingested material from a stomach of a patient fitted with an external gastrostomy connection to the stomach. This method includes: coupling a siphon tube to the connection so as to create a siphon system having an aggregate length in excess of 25 cm; and draining content of the stomach through the siphon tube.

Another application of some of the above-described embodiments is to implement a method of removing ingested material from a stomach of a patient fitted with an external gastrostomy connection to the stomach. This method includes the steps of: pumping a fluid through the connection into the stomach to increase fluid in the stomach without ingestion of fluid; and draining content of the stomach through the connection. Optionally, the fluid may include one or more of the following: water, a nutrient, a medication, and returned gastric juices.

Another application of some of the above-described embodiments is to implement an apparatus for removing ingested material from a stomach of a patient fitted with an external gastrostomy connection to the stomach. This apparatus includes: a fluid source for infusing fluid into the stomach through the connection; and a drain line for draining content of the stomach received from the connection. Optionally, a siphon system is used for passively draining content of the stomach, preferably using flat tubing. Optionally, a pump may be coupled to the fluid source for pumping fluid through the connection into the stomach.

Another application of some of the above-described embodiments is to implement a method of removing ingested food from a patient's stomach via a gastrostomy tube that passes through the patient's abdominal wall into the patient's stomach. This method includes the steps of: (a) extracting a portion of the matter contained in the patient's stomach via the gastrostomy tube; (b) removing stomach acid from the matter extracted in the extracting step; and (c) returning the stomach acid removed in the removing step to the patient's stomach via the gastrostomy tube. Optionally, the removing step includes the steps of: (i) filtering out solid portions from the matter extracted in the extracting step; and (ii) filtering a liquid resulting from step (i) using a semi-permeable membrane or an anionic exchange membrane. In this application, the extracting step may be implemented by siphoning or pumping.

Another application of some of the above-described embodiments is to implement an apparatus for removing food from a patient's stomach via a gastrostomy tube that passes through the patient's abdominal wall into the patient's stomach. This apparatus includes: a connector configured to connect to a proximal end of the gastrostomy tube with a fluid-tight connection; a filter configured to separate stomach acid from other matter; a first path from the connector to the filter, configured to route matter extracted from the patient's stomach into the filter; a pump configured to pump stomach acid that has been separated by the filter back into the patient's stomach; and a second path configured to route the other matter to a waste outlet. In this application, the matter extracted from the patient's stomach may be routed into the filter by pumping or siphoning. Optionally, this apparatus may further include a reservoir configured to hold liquid and a pump configured to pump the liquid from the reservoir into the patient's stomach via the connector.

Another application of some of the above-described embodiments is to implement a method of removing ingested food from a patient's stomach via a gastrostomy tube that passes through the patient's abdominal wall into the patient's stomach. This method includes the steps of: providing an apparatus for siphoning or pumping ingested food out of the patient's stomach via the gastrostomy tube; and limiting the number of times that the siphoning or pumping operation can be performed by the apparatus. The number of times that the siphoning or pumping operation can be performed may be limited by a variety of factors such as (a) elapsed time from a first use, (b) how many times siphoning or pumping of food has been performed, (c) how many times the apparatus has been connected to the gastrostomy tube, or (d) the volume of matter that has been extracted from the patient's stomach. Optionally, this method may further include the step of infusing liquid into the patient's stomach via the gastrostomy tube, wherein the infusing step is performed in alternation with the siphoning or pumping.

Another application of some of the above-described embodiments is to implement an apparatus for removing food from a patient's stomach via a gastrostomy tube that passes through the patient's abdominal wall into the patient's stomach. This apparatus includes: a connector configured to connect to a proximal end of the gastrostomy tube with a fluid-tight connection; and a first fluid path provided between the connector and a drain port, configured to permit, for a limited number of times only, siphoning or pumping food from the patient's stomach out to the drain port. The number of times that the siphoning or pumping can be performed may be limited by a variety of factors such as (a) elapsed time from a first use, (b) how many times siphoning or pumping of food has been performed, (c) how many times the apparatus has been connected to the gastrostomy tube, or (d) the volume of matter that has been extracted from the patient's stomach. Optionally, this apparatus may further include: a reservoir for holding liquid to be infused into the patient's stomach; a second fluid path from the reservoir to the connector, configured to permit infusion of the liquid in the reservoir into the patient's stomach; and a fluid circuit configured to alternately (a) open the first fluid path during a first interval of time to permit siphoning or pumping food from the patient's stomach and (b) open the second fluid path during a second interval of time to permit infusion of the liquid in the reservoir into the patient's stomach.

Note that while the system is described herein in the context of removing the ingested material from the patient's stomach, it can also be used to remove the ingested material from other portions of the patient's upper digestive tract (e.g., the jejunum).

Although the above discussion discloses various exemplary embodiments of the invention, it should be apparent that those skilled in the art can make variations and modifications that will achieve some of the advantages of the invention without departing from the true scope of the invention. Accordingly, other embodiments are within the scope of the following claims.

We claim:

1. A valve assembly for alternately providing and preventing the passage of fluid and food through a fluid pathway comprising:
    a bottom platform having a first thru-hole biased to one quadrant;
    a top platform having a second thru-hole biased to one quadrant;
    a middle layer having a third thru-hole biased to one quadrant, the middle layer comprising an elastomeric material and being sandwiched between the bottom platform and the top platform; and
    a retainer configured to retain the bottom platform in proximity to the middle layer and top platform such that the middle layer and top platform can be moved together with respect to the bottom platform between a first position and a second position, wherein in the first position the first, second, and third thru-holes align to provide access to the fluid pathway and in the second position the first, second and third thru-holes are not aligned to provide a fluid tight seal and to prevent passage of fluid and food through the fluid pathway; wherein
    the first thru-hole of the valve assembly is configured to mate with and remain stationary with respect to a gastrostomy tube.

2. The valve assembly according to claim 1, the bottom platform being configured to sit against a patient's skin.

3. The valve assembly according to claim 1, the first, second and third thru-holes each having a diameter from about 6 to about 8 mm.

4. The valve assembly according to claim 1, each platform having a diameter from about 3.5 to about 7 times larger than diameter of the thru-hole that passes therethrough.

5. The valve assembly according to claim 1, the middle layer being sandwiched between the top platform and bottom platform with a force that is high enough to prevent leaks and yet low enough to permit movement of the middle layer with respect to the bottom platform.

6. The valve assembly according to claim 1, the middle layer being attached to the top platform.

7. The valve assembly according to claim 1, one platform being capable of moving with respect to the other platform by a rotational force.

8. The valve assembly according to claim 1, one platform being capable of moving in a generally linear direction with respect to the other platform.

9. The valve assembly according to claim 1, the valve assembly being configured to provide access to the fluid pathway without changing the internal diameter of the fluid pathway.

10. An apparatus comprising:
    a valve assembly for alternately providing and preventing the passage of fluid and food through a fluid pathway comprising:
        a bottom platform having a first thru-hole biased to one quadrant;
        a top platform having a second thru-hole biased to one quadrant,
        a middle layer having a third thru-hole biased to one quadrant, the middle layer comprising an elastomeric material and being sandwiched between the bottom platform and the top platform; and
        a retainer configured to retain the bottom platform in proximity to the middle layer and top platform such that the middle layer and top platform can be moved together with respect to the bottom platform between a first position and a second position, wherein in the first position the first, second, and third thru-holes align to provide access to a fluid pathway and in the second position the first, second and third thru-holes are not aligned to provide a fluid tight seal and to prevent passage of fluid and food through the fluid pathway; and
    a gastrostomy tube having a distal end and a proximal end;
    the first thru-hole of the valve assembly being mated with and remaining stationary with respect to the proximal end of the gastrostomy tube.

11. The apparatus according to claim 10, the fluid pathway comprising a uniformly sized lumen extending from a gastrostomy tube through the valve assembly.

12. The apparatus according to claim 11, the lumen having a sufficiently large diameter to accommodate food particles.

13. The apparatus of claim 10, wherein the middle layer is attached to the top platform by an adhesive.

14. The apparatus of claim 10, wherein the middle layer and top platform can be rotated together with respect to the bottom platform.

15. An apparatus for providing and preventing access to a fluid pathway of a gastrostomy tube that passes through a patient's abdominal wall into the patient's stomach, the apparatus comprising:
    a first connector comprising a valve assembly, the valve assembly comprising:

a first platform having a first thru-hole biased to one quadrant, the first platform being mounted to a gastrostomy tube so as to remain stationary with respect to the gastrostomy tube and to provide a fluid pathway directly between the gastrostomy tube and the first thru-hole, a second platform having a second thru-hole biased to one quadrant, a third platform having a third thru-hole biased to one quadrant, the third platform being sandwiched between the first and second platforms and being fixed with respect to the second platform such that the third thru-hole is aligned with the second thru-hole, and a retainer that retains the first platform in proximity to the second platform such that the second platform can be rotated with respect to the first platform between a first position wherein the first and second thru-holes align to provide access to the fluid pathway of the gastrostomy tube and a second position wherein the first and second thru-holes offset to prevent access to the fluid pathway of the gastrostomy tube, the connector being configured for flush mounting on a patient's skin and having a low profile with respect to the patient's skin.

16. The apparatus of claim 15, the first connector further comprising a skin flange, the skin flange being capable of interfacing with the first platform, sitting flush against a patient's skin and being connected to a gastrostomy tube positioned in a patient.

17. The apparatus of claim 16 further comprising one or more protrusions disposed on the first platform that fasten to one or more complementary recesses in the skin flange.

18. The apparatus of claim 15 further comprising:

a second connector having a disk defining a disk thru-hole sized and positioned to complement the first and second thru-hole and one or more protrusions that removably couple to one or more structures disposed on the first connector.

19. The apparatus of claim 18 where the second connector further comprises a ridge configured to mate with a valley on the first connector.

20. The apparatus of claim 18 wherein the second connector further comprises a tube having a second fluid pathway that couples to the disk thru-hole.

21. The apparatus of claim 20 wherein the fluid pathway and the second fluid pathway are joined when the first and second thru-holes align in the first position.

22. The apparatus of claim 18 wherein the first and second thru-holes align in the first position to provide access to the fluid pathway when the second connector is coupled to the first connector.

23. The apparatus of claim 18 wherein the first and second thru-holes are offset in the second position to prevent access to the fluid pathway when the second connector is separate from the first connector.

24. The apparatus of claim 15 wherein aligning the first and second thru-holes in the first position avoids restriction of the gastrostomy tube.

25. The apparatus of claim 15 wherein the first platform further comprises a spout surrounding at least a portion of the first thru-hole, the spout being sized to enter the lumen at the proximal end of the gastrostomy tube.

26. The apparatus according to claim 15, the first, second and third thru-holes each having a diameter from about 6 to about 8 mm.

27. The apparatus according to claim 15, the first, second and third platforms each having a diameter from about 3.5 to about 7 times larger than the diameter of the thru-hole.

28. The apparatus according to claim 15, the third platform being sandwiched between the first platform and second platform with a force that is high enough to prevent leaks and yet low enough to permit movement of the third platform with respect to the first platform.

29. The apparatus according to claim 15, the third platform comprising an elastomeric material.

30. The apparatus according to claim 15, the valve assembly being configured to provide access to the fluid pathway without changing the internal diameter of the fluid pathway.

31. The apparatus of claim 15, wherein the low profile measures between about 5 and about 20 mm.

32. The apparatus of claim 15, wherein the low profile measures between about 7 and about 9 mm.

33. The apparatus of claim 15, wherein the first platform directly contacts the patient's skin.

34. The apparatus of claim 15, further comprising an outer skirt that surrounds the first connector and tapers down towards the patient's skin at the periphery of the outer skirt.

35. The apparatus of claim 34, wherein the outer skirt comprises a soft, compliant material.

36. The apparatus of claim 34, wherein the outer skirt comprises an elastomer.

37. The apparatus of claim 34, wherein the outer skirt comprises a foam material.

38. The apparatus of claim 15, wherein the third platform is attached to the second platform by an adhesive.

* * * * *